US008388530B2

(12) United States Patent
Shusterman

(10) Patent No.: US 8,388,530 B2
(45) Date of Patent: Mar. 5, 2013

(54) PERSONALIZED MONITORING AND HEALTHCARE INFORMATION MANAGEMENT USING PHYSIOLOGICAL BASIS FUNCTIONS

(76) Inventor: Vladimir Shusterman, Pittsburgh, PA (US)

( * ) Notice: Subject to any disclaimer, the term of this patent is extended or adjusted under 35 U.S.C. 154(b) by 219 days.

(21) Appl. No.: 12/885,520

(22) Filed: Sep. 19, 2010

(65) Prior Publication Data

US 2011/0004110 A1 Jan. 6, 2011

Related U.S. Application Data

(63) Continuation-in-part of application No. 11/641,268, filed on Dec. 20, 2006, now Pat. No. 7,801,591, which is a continuation-in-part of application No. 10/816,638, filed on Apr. 2, 2004, now Pat. No. 7,343,197, which is a continuation-in-part of (Continued)

(51) Int. Cl.
*A61N 1/00* (2006.01)
(52) U.S. Cl. ...................................... 600/300; 600/509
(58) Field of Classification Search .................. 600/300, 600/508–523
See application file for complete search history.

(56) References Cited

U.S. PATENT DOCUMENTS

| | | | |
|---|---|---|---|
| 4,193,393 A | 3/1980 | Schlager | |
| 4,679,144 A | 7/1987 | Cox et al. | |
| 5,033,475 A | 7/1991 | Ueda et al. | |
| 5,463,548 A | 10/1995 | Asada et al. | |
| 5,501,229 A | 3/1996 | Selker et al. | |
| 5,544,044 A | 8/1996 | Leatherman | |
| 5,724,983 A | 3/1998 | Selker et al. | |
| 5,876,353 A | 3/1999 | Riff | |
| 5,941,820 A | 8/1999 | Zimmerman | |
| 5,956,013 A | 9/1999 | Raj et al. | |
| 5,967,995 A | 10/1999 | Shusterman et al. | |
| 6,038,469 A | 3/2000 | Karlsson et al. | |
| 6,108,635 A | 8/2000 | Herren et al. | |
| 6,126,596 A | 10/2000 | Freedman | |
| 6,154,668 A | 11/2000 | Pedersen et al. | |

(Continued)

OTHER PUBLICATIONS

V. Shusterman et al., Building and Application of Expert Systems for Differential Diagnostics of Cardiovascular Diseases, SAMS 1994, vol. 14, pp. 15-24.

(Continued)

*Primary Examiner* — Scott Getzow

(57) ABSTRACT

Analysis of individual's serial changes, also referred to as the physiological, pathophysiological, medical or health dynamics, is the backbone of medical diagnosis, monitoring and patient healthcare management. However, such an analysis is complicated by enormous intra-individual and inter-individual variability. To address this problem, a novel serial-analysis method and system based on the concept of personalized basis functions (PBFs) is disclosed. Due to more accurate reference information provided by the PBFs, individual's changes associated with specific physiological activity or a sequence, transition or combination of activities (for example, a transition from sleep to wakefulness and transition from rest to exercise) can be monitored more accurately. Hence, subtle but clinically important changes can be detected earlier than using other methods. A library of individual's PBFs and their transition probabilities (which can be described by Hidden Markov Models) can completely describe individual's physiological dynamics. The system can be adapted for healthcare information management, diagnosis, medical decision support, treatment and side-effect control. It can also be adapted for guiding health, fitness and wellness training, subject identification and more efficient management of clinical trials.

20 Claims, 9 Drawing Sheets

Related U.S. Application Data application No. 10/124,651, filed on Apr. 17, 2002, now Pat. No. 6,925,324, which is a continuation-in-part of application No. 09/583,668, filed on May 30, 2000, now Pat. No. 6,389,308.

(56) References Cited

U.S. PATENT DOCUMENTS

| | | |
|---|---|---|
| 6,188,988 B1 | 2/2001 | Barry et al. |
| 6,221,011 B1 | 4/2001 | Bardy |
| 6,312,378 B1 | 11/2001 | Bardy |
| 6,336,903 B1 | 1/2002 | Bardy |
| 6,368,284 B1 | 4/2002 | Bardy |
| 6,440,066 B1 | 8/2002 | Bardy |
| 6,480,111 B2 | 11/2002 | Canady et al. |
| 6,681,131 B2 | 1/2004 | Kandori et al. |
| 6,807,438 B1 | 10/2004 | Brun Del Re et al. |
| 2004/0232912 A1 | 11/2004 | Tsukamoto et al. |
| 2010/0049069 A1 | 2/2010 | Tarassenko et al. |
| 2010/0056939 A1 | 3/2010 | Tarassenko et al. |

OTHER PUBLICATIONS

Batchvarov et al., QT-RR relationship in healthy subjects exhibits substantial intersubject variability and high intrasubject stability, Am J Physiol 282: H2356-H2363, 2002.

Malik et al., Relation between QT and RR intervals is highly individual among healthy subjects: implications for heart rate correction of the QT interval, Heart 2002; 87 220-228.

PERSONALIZED MONITORING AND HEALTHCARE INFORMATION MANAGEMENT USING PHYSIOLOGICAL BASIS FUNCTIONS

CROSS-REFERENCE TO RELATED APPLICATION

This is a continuation-in-part of application Ser. No. 11/641,268 filed Dec. 20, 2006, which was a continuation-in-part of application Ser. No. 10/816,638, filed Apr. 2, 2004, now U.S. Pat. No. 7,343,197, which was a continuation-in-part of application Ser. No. 10/124,651, filed Apr. 17, 2002, now U.S. Pat. No. 6,925,324, which was a continuation-in-part of application Ser. No. 09/583,668, filed May 30, 2000, now U.S. Pat. No. 6,389,308.

FIELD OF THE INVENTION

This invention relates to the field of medical monitoring, healthcare information management, diagnosis, and decision support and more specifically to a method and system for personalized monitoring and analyzing of medical or health data, optimizing the information flow, structuring and representing the results.

BACKGROUND OF THE INVENTION

Biomedical data are quasi-periodic, which means that patterns of biological activity are repetitive to some extent, but each cycle of repetition is slightly different. Some examples of repetitive patterns include heart beats and associated electrocardiographic (ECG) waveforms, which consist of a sequence of waveforms, referred to as the P, Q, R, S, and T-waves. Yet, the duration and amplitudes of these waveforms change from beat to beat, and certain types of changes signify development of a heart disease or non-cardiac physiological disorder. An accurate analysis of changes in the amplitudes and durations of the ECG waveforms is important for medical diagnosis, detecting changes in someone's health or fitness level. Therefore, analysis of these ECG waveforms is the 1$^{st}$ step of a standard diagnostic ECG analysis, which is commonly used in clinical practice. A number of algorithms have been developed for the detection and classification of such ECG waveforms in the diagnostic 12-lead ECG, ambulatory (Holter) recordings, telemetry recordings or implantable devices, using various filters, template matching, wavelet transform, Markov, hidden Markov models, and neural networks. However, analysis of serial changes in such waveforms remains challenging due to the following reasons. First, the changes may be slow or gradual, escaping detection by traditional, visual analysis or simple statistical tests (such as a simple comparison with a threshold value). Second, many individuals already have pre-existing abnormalities in their medical data. For example, patients with chronic heart disease often have a persistent deviation of the level of electrocardiographic ST-segment from the isoelectric line. This makes identification of new, more recent changes in the ST-segment difficult in such patients, and simple statistical tests (for example, comparison with an average threshold value) may not detect acute changes masked by pre-existing, abnormal patterns. Finally, the identification and classification of physiological patterns is obscured by a large number of external (environmental) and internal (physiological, biochemical, biophysical, genetic, etc.) modulating factors.

Other types of repetitive patterns which are important for medical diagnosis and patient management include: i) respiratory movements or breathing patterns, which exhibit a variety of changes during physical or mental stress, and may become irregular during sleep (also referred to as the sleep disordered breathing or sleep apnea); ii) circadian (day-night) variations in physiological activity, including physical activity, metabolism, heart rate and blood pressure; such circadian rhythmicity has been observed in a number of clinical events and complications, for example, the morning rise in the incidence of myocardial infarction, sudden death and ventricular tachyarrhythmias, in contrast to the nocturnal rise in the incidence of paroxysmal atrial fibrillation; iii) seasonal variations in the incidence, severity and complications of chronic diseases (for example, an increase in the number of complications associated with the duodenal ulcers in the spring and fall seasons).

Another example of a repetitive signal is beat-to-beat alterations in the amplitude of the T-wave (referred to as the T-wave alternans or TWA), which may indicate heightened risk of sudden death. TWA are also affected by changes in heart rate, physiological and neurohormonal activity, respiration and other modulating factors, which obscure their accurate analysis.

Tracking changes in health or medical data, using individual's own data as a personalized reference, allows one to improve the accuracy of medical diagnosis. Comparing current data with individual's historical test results, such as previous electrocardiogram (ECG), blood pressure, heart rate, cardiac output, intra-thoracic fluid or transthoracic impedance, helps physicians in differentiating acute changes, which usually require proactive management, from chronic abnormalities. In addition, comparison with individual's historical data also helps in exposing subtle or gradual changes. For example, patients with chronic ischemic heart disease often have gradual narrowing of coronary arteries, which is associated with gradual, subtle changes in the electrocardiographic STT-complex, which are difficult to detect. Other symptoms may include slowly diminishing tolerance to physical exercise, which can also be difficult to detect. In the absence of individual's historical data, physicians often rely on population-derived statistical averages, which may not be applicable to a particular individual and may lead to incomplete or inaccurate diagnosis.

SUMMARY OF THE INVENTION

This application further extends Shusterman patents on multi-scale serial analysis described above, by introducing physiological basis functions (also referred to as PBFs, baseline, reference, or physiological templates) for more accurate tracking of individual's dynamics and more accurate detection and classification of individual's physiological waveforms, such as electrocardiographic P, Q, R, S, T and U-waves described above.

Shusterman patent application Ser. No. 11/641,268 filed Dec. 20, 2006, and U.S. Pat. Nos. 7,485,095, 7,343,197, 6,925,324, and 6,389,308 have shown that personalized, individually "tailored" analysis provides superior accuracy compared to population-derived estimates. The disclosures contained in those Shusterman patents and application are, by reference, incorporated herein in their entireties. More recently, these results have been confirmed by other researchers. For example, Batcharov et al. described high accuracy (assessed by the stability of the estimates based on individual's data) in contrast to low accuracy of the population-based average estimates for QT-RR relationship. (Batcharov V N, Ghuran A, Smetana P, Hnatkova K, Harries M, Dilaveris P, Camm A J, Malik M. QT-RR relationship in healthy subjects exhibits substantial intersubject variability and high intrasubject stability. *Am J Physiol Heart Circ Physiol* 2002; 282: H2356-H2363; Malik M, Färbom P, Batchvarov V, Hnatkova K, Camm A J. Relation between QT and RR intervals is highly individual among healthy subjects: implications for heart rate correction of the QT interval. Heart 2002; 87:220-228.)

Among traditional statistical methods that are commonly used for the analysis of serial changes are paired tests and repeated-measures Analysis of Variance (ANOVA). Neither method, however, can account for complex individual patterns of serial dynamics. Analysis of such complex serial changes requires specialized statistical time-series or signal processing methods, which have been disclosed by Shusterman in the application Ser. No. 11/641,268 filed Dec. 20, 2006, and U.S. Pat. Nos. 7,485,095, 7,343,197, 6,925,324, and 6,389,308. In this application, Shusterman disclosed how these methods can be adapted for the detailed characterization of individual's physiological dynamics, such as serial changes in ECG, blood pressure, cardiac output or intra-thoracic fluid. These methods may include mathematical decomposition, time-series analysis, mathematical modeling, computer modeling, signal processing, statistical analysis, and methods of artificial intelligence. Some examples of specific methods include hidden Markov models, orthogonal decomposition, non-orthogonal decomposition (independent component analysis), multidimensional scaling based on non-metric distances and mapping techniques, non-orthogonal linear mappings, nonlinear mappings and other methods, that make use of projection, re-scaling (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability and Mahalanobis distance, pattern recognition, fuzzy logic, neural networks, expert systems, and hybrid artificial intelligence systems.

Use of PBFs in accordance with this invention is fundamentally different from the methods for detection and classification of individual waveforms described above, because PBFs use the time series comprised of individual waveforms (rather than individual waveforms used in standard methods) collected over at least several seconds and, preferably, over longer time intervals (minutes, hours, days, weeks, months, years) and have the following properties:

1) PBF includes serial data or its characteristic elements (e.g., time series of ECG waveforms, heart rate, electrocardiographic P, Q, R, S, T and U waves, QRS-complex, QT-interval, ST-segment, arterial pressure waves, cardiac output, respiration);
2) PBF is associated with a specific physiological activity (such as sleep, REM-sleep, non-REM sleep, wakefulness, physical exercise, food intake, swimming, mental stress), or sequence of activities (transition from sleep to wakefulness, sequence of rest, exercise, return to rest, sequence of baseline, stress, and post-stress period).
3) PBF may have several time scales (multi-scale structure). For example, a PBF representing 24-hour physiological cycle may include shorter PBFs representing sleep, transition from sleep to wakefulness, exercise, food intake, and rest states. Another example of a multi-scale PBF is a seasonal PBF, which would include multiple 24-hour PBFs.
4) PBF can be individually adapted or "tailored" to the specifics of individual's data;
5) PBF can be further adjusted by using statistical (population-based) data related to age, gender, weight, medical history and other distributions;
6) PBF can include several types of information (also referred to as the information fusion); for example, a multi-signal, composite PBF may include simultaneously collected ECG, respiratory movements, blood pressure, cardiac output, intra-thoracic fluid volume, vascular resistance, and physical activity. Another example of a composite PBF for tracking individual's sleep patterns may include individual's respiratory amplitude and frequency, changes in heart rate, electroencephalogram and muscular activity during REM and non-REM sleep.
7) The time series of data comprising PBFs can be characterized by at least one of mathematical, statistical, modeling and computational methods described in the Shusterman patents listed above, which are incorporated herein by reference, and either PBFs or their characteristics can be used as a personalized reference for tracking changes in newly acquired data and improving detection and classification of physiological waveforms (e.g., electrocardiographic P, Q, R, S, T, U-waves, QRS-complex, arterial pressure waves, respiration).

This invention provides a method and system that can be used for at least one of information management, decision support, and diagnosis. The method and system distribute (structure) the information into at least two levels of detail (scales or resolutions). A low-resolution scale represents a snapshot measurement of at least one indicator (vital sign or primary element) such as heart rate or blood pressure. A higher resolution scale is designed to determine serial changes in each of the said primary elements. Low, intermediate and high-resolution scales can exchange information between each other for improving the analyses; the scales can be distributed vertically among the units connected by a network and defined according to the corresponding software and hardware resources. Uncertainty or probability of a diagnosis is tracked dynamically (the probabilities are updated periodically or quasi-periodically over time taking into account information available at each time point; new information is included in the analysis as it becomes available) based on the information availability or completeness relative to the total complete information at each level and at multiple levels. This structuring provides several advantages. First, it improves and optimizes the flow of information along the network. This feature is significant, since the volume of information provided by a multitude of diagnostic tests is high (such as electrocardiographic monitoring, magnetic resonance imaging (MRI), computer tomography (CT), CAT-scans, echocardiography, biochemical, and other tests) and increases with time. The structuring permits control this high volume of information, so the most important information (vital signs) is analyzed on-line and on-site (Low-resolution), whereas the rest of the information, which includes subtle changes in patient's state, are detected and quantified using comparative analysis of serial data (Higher level of resolution). Such distribution of the enormous amount of medical information prevents information overload and ensures that the information is processed accurately and in a timely fashion, and allow medical professionals to receive adequate and accurate information about the patient tailored to the specific setting of the medical care and patient's profile.

Second, this multi-level structure also ensures adaptability of the system, in which the system processes all available data to learn the individual patient's pattern of normal range and abnormal variations. The adaptability is achieved by collecting and processing serial data at the higher scales and then, using this information at the lower scale to individually tailor (edit, adjust) the diagnostic and processing criteria (thresholds). Third, for reasons described above, this multi-level structure also optimizes bi-directional communication and personalized and timely advice and treatment of each patient.

Thus, by vertically distributing the analyses and representation in several levels, the system optimizes information flow, usage of medical knowledge, and improves accuracy of analysis of serial changes, and adaptability to each individual's data. Low, intermediate and high-resolution scales can exchange information between each other for improving the analyses; the scales can be distributed among the units connected by a network and defined according to the corresponding software and hardware resources. In addition, the system can be adapted to optimize usage of medical knowledge contained in medical journals, books, the Internet, and other materials for personalized analysis of serial data. The system optimizes and improves the information flow by vertically distributing it into several levels or Scales according to the importance and relevance of the information, and according to the available software and hardware resources. The low-resolution Scale I represents one-time, periodic, or quasi-periodic snapshot measurements of health data, such as heart rate, blood pressure, blood count, cardiac output, physical activity, temperature, and weight, referred to as the primary elements. The higher-resolution Scale II is used to analyze serial changes in each of these primary elements. Optionally, the $3^{rd}$ scale can be used to analyze combined serial changes of these primary elements. By using this personalized analysis, the system improves accuracy and clarity of analysis and representation of personalized serial analysis. These scales can also include medical knowledge from medical textbooks, journals, and other materials available on the computer network to improve personalized analysis.

Examples of such a multi-scale structure for analysis, representation, distribution and management of health data is presented in FIG. 1. As depicted in the figure, in the first (bottom) scale, data is collected from at least one, and preferably, a multitude of diagnostic devices, such as electrocardiographic, electroencephalographic, echocardiographic, magnetocardiographic, magnetic resonance imaging, computer tomography, thermometer, blood pressure tonometer, pulse oxymeter, impedance meter, genetic/DNA/genotype/proteomics/metabolomics measurements, MRI, CT, ultrasound, fluoroscopic, X-ray image, stress-test, physical activity test, neurographic recordings, biochemical tests, blood tests, enzyme tests, clinical symptoms, such as chest pain, shortness of breath, nausea, etc. These data can be collected as a one-time test, periodic, quasi-periodic, or continuous monitoring (measurements). At the low-resolution level (scale) I, these data are processed to extract the most important indicators (vital signs, diagnostic indicators) or primary elements, such as heart rate, blood pressure, magnitudes and durations of electrocardiographic waves (QRS, T, and P-waves, and ST-segment, T-wave alternans), cardiac output, respiration, temperature, neural activity, etc.

At the next level (scale) II, dynamics of each primary element (vital sign or diagnostic indicator) is analyzed using serial recordings obtained from the individual. The dynamical (serial) analysis is performed using the mathematical, modeling, probabilistic, pattern-recognition, time-series, signal-processing, statistical, computer, and artificial intelligence methods described below. In the simplest-case scenario, serial changes are analyzed using simple statistical parameters, such as the mean or median value, or the standard deviation (a square root of variance), or a range of variations (for example, 25%-75% range) of the time series of serial changes over a certain time interval. The serial changes in any of these statistical parameters or in the combination of these parameters can be estimated, for example, using a statistical test that determines the statistical significance of serial changes over time (for example, a non-parametric, Friedman ANOVA for repeated measurements or a paired t-test, or an ANOVA for repeated measurements), or using pre-selected or adaptive thresholds (for example, a threshold of 3 standard deviations can be used to detect significant changes in the mean values). As a result of this dynamic analysis, trends of changes are represented either as quantitative data, qualitative information, an advice, or graphs of trends in genetic, genomic, proteomic, electrocardiographic, echocardiographic, neurographic (neural), electroencephalographic, magnetocardiographic, magnetoencephalographic, magnetic resonance (MRI), computer tomography (CT) and X-ray imaging. The results of analysis can be also color-coded, for example, if an indicator is within a normal range or within a certain percent of a moving average of previous values, it will be highlighted with a green color. A borderline parameter can be highlighted by yellow color, and a parameter beyond 3 standard deviations from normal range can be highlighted by red color.

The results of dynamic analysis performed at Scale (level) II are sent to the next, third level of processing. They are also sent to the Level I to personalize (adjust, adapt, individually tailor) the diagnostic thresholds. For example, the threshold for detection of tachycardia can be lowered if the subject's individual heart rate during the last several days was slow. Or the threshold for detection of QT-prolongation could be lowered if the subject is taking antiarrhythmic drugs that prolong QT interval.

When the information is transferred to the Level III, dynamics of each vital sign (primary element, diagnostic indicator) is integrated to generate a combined personalized dynamics that includes changes (trends) of various diagnostic indicators. Combining the information or using parameter fusion (when several parameters are combined into a single, composite parameter) improves the diagnostic value of the information, since a combination of parameters can help to achieve a more accurate diagnosis. For example, combination of trends of heart rate and T-wave alternans can be used to determine at which level of heart rate T-wave alternans increase and at which level of heart rate T-wave alternans disappears. Another example is a combined analysis of changes in heart rate and QT-intervals, which allows determining a personalized relationship between these two values. This combined information can be useful for determining an optimal treatment strategy, for example, whether or not the level of T-wave alternans at a given heart rate is abnormal and should be controlled, for example, by implanting an implantable cardioverter-defibrillator (ICD). The results obtained using this combined analysis at Level III are sent to the higher scale and to the lower scales II and I for individual tailoring (personalized adaptation or adjustment) of diagnostic criteria (thresholds).

At Level IV, the results of information processing performed at lower levels I-III are compared with medical knowledge available in medical textbooks, scientific journals, databases, Internet, networks, and libraries, including statistical data, guidelines, and case studies to determine possible diagnoses. The comparison with medical knowledge can be performed using statistical analysis, pattern recognition, artificial intelligence, neural networks, expert systems, mathematical decomposition, mathematical transformation, or mathematical modeling or computer modeling. As a result of this comparison, a list of possible causes of patient's symptoms is determined along with the probability of each diagnosis. This information is sent to the next, Level V, which determines the most probable diagnosis.

Note that the multi-scale (multi-layer) structure can be compressed into fewer (even 2) scales (that can be implemented in the a single microprocessor, computer, cell phone, PDA, smart phone, microcontroller) or expanded into more scales (which can be also distributed among several different parallel or hierarchical databases connected via network or Internet), depending on the specifics of a clinical setup, available hardware and software resources, and depending on the specifics of an individual patient health status and personal profile, including age, diagnosis, disease stage, etc. It is also possible to use any number or combination of the above-described (or similar) levels (layers, scales). For example, a specific diagnostic structure can be used for subjects with chronic congestive heart failure with a typical profile of a low ejection fraction, a low tolerance to physical activity, relatively high resting heart rate and low heart rate variability. Among the parameters that could be modified for such patients is a narrow range of normal heart rate variations. At each scale, the analysis can use at least one of statistical methods, probabilistic methods, Bayesian models/networks, Markov models or hidden Markov models, pattern recognition, artificial intelligence, neural networks, expert systems, mathematical decomposition, mathematical transformation, or mathematical modeling or computer modeling.

FIG. 2 shows another variant of multi-scale structure, in which the $1^{st}$ level, low-resolution analysis is implemented together with each diagnostic sensor, so that collecting health data and processing these data in a low-resolution, $1^{st}$ level analysis is done at the same place, in a real-time. The collected heath data and/or the results of $1^{st}$-level processing are then sent to the $2^{nd}$ level processing, possibly, via Bluetooth, other radio-transmitters, cell phone, Wi-Fi or other networks. The $2^{nd}$ level processing, as explained earlier, includes analysis of serial changes, using the information obtained previously from the same subject, and sends the results of analysis back to the $1^{st}$ level to optimize diagnostic and monitoring thresholds.

FIG. 3 shows yet another version of a multiscale structure, in which Scale 2 analysis is also distributed among different locations. The $2^{nd}$ scale analysis can be implemented on-site within the same diagnostic unit that collects health data and performs $1^{st}$ scale analysis. Alternatively, the $2^{nd}$ scale analysis can be implemented at a different physical location, or distributed among several different locations, as FIG. 3 shows.

Note also that the multi-scale structure can be further expanded in horizontal direction, to include different modules of support for different groups of diseases (for example, modules for cardiovascular, neurological, gastroenterological, infectious disease), different patient populations (heart failure, renal failure, chronic obstructive lung disease, elderly, etc.), different groups of medications (anti-arrhythmic, beta-blockers, etc), different device treatments (implantable cardiac devices, hemodialysis, etc.), different medical settings (ambulatory, inhospital, out-of-hospital, military, mass emergency situations, terrorist threats, weapons of mass destruction alerts).

The multi-scale structure can be implemented in various combinations of computing devices, such as cell phones, specialized processors, personal digital assistant (PDA), smart phone, personal computer, a computer network or specialized networks. It is possible, for example, to implement the first 2 or 3 scales in a miniaturized, personal system (for example, implemented in a cell phone or a personalized monitoring system) that a person carries around, whereas the higher levels are implemented in a computing device that is located remotely and communicates with the lower levels by using wireless communication (cell phone, GPS, GPRS, Internet, Wi-Fi, etc.). Other combinations of scales implemented locally or at remote locations are also possible. Preferably, the higher-level analysis is performed on a powerful computer device, such as a computer server, which has a database of serial data from each subject for comparative analysis, and also a database of medical knowledge of characteristics of different diseases. Another example of implementation of a multi-level structure is a home system, which includes sensors (can be embedded in home appliances, such as bed, chairs); lower and higher-level processing units implemented in a home computer (which can also communicate information to and from an individual via a TV or radio or cell phone) and a higher-level processing (connected via Internet or specialized network) implemented in a medical center. Yet, another example of implementation of a multi-level structure is a car-based system, which includes sensors for physiological monitoring or periodic checkups, (i.e. sensors for monitoring heart rhythm could be incorporated in the armchair; other sensors might be activated and attached to the human body whenever necessary). The sensors are connected with the car's computer (the connection could be wireless, via Bluetooth or Zigbee), so that the computer can perform the $1^{st}$ scale processing or both, the $1^{st}$ and $2^{nd}$ scale processing. Alternatively, the sensors can communicate directly with a cell phone, which performs the $1^{st}$ or $1^{st}$ and $2^{nd}$ scale processing. The cell phone (or the car computer) can be connected wirelessly (via a cell phone, GPS, or Internet) with a remote computer (which contains a database of this person's serial recordings) for a higher-level processing. Each of these processing levels has a bi-directional communication with other levels for exchanging information, individual tailoring of monitored parameters, providing advice or warnings to the individual in the car or sending an alarm/notification to the individual's physician or nurse via a cell phone or remote computer.

The above-described structure can be used for forecasting (prediction) of the trends in patient's status, including forecasting high-risk periods for developing myocardial ischemia or cardiac arrhythmias by analyzing changes in the pattern of physiological indicators and determining periods when these patterns become unusual (for example, exceeding 3 standard deviations of normal range) or abnormal and, therefore, indicating high-risk of a complication, such as myocardial infarction, arrhythmia, or stroke. The prediction can be performed using at least one of statistical methods, probabilistic methods, Markov models, hidden Markov models, Bayesian network, pattern recognition, artificial intelligence, neural networks, expert systems, mathematical decomposition, mathematical transformation, or mathematical modeling or computer modeling.

The above-described system can be also used to provide an advice or a recommendation regarding changes in diet, stress management, physical activity, treatment (for example, administering a drug or implanting an implantable cardioverter-defibrillator or pacemaker device), or a necessity of diagnostic test. The system can also be used for bi-directional communication between individual subjects (patients), medical centers, and medical professionals (physicians, nurses, and technicians). The above-described system can be also integrated into other information management systems, for example, standard data management systems (such as hospital information management systems). The system can represent the results using at least one of quantitative presentation for medical professionals and qualitative presentation for a lay person who has no medical background. Structuring of the analysis is achieved by constructing the at least two, and preferably three, information scales that represent the most significant parameters at different level of detail.

In the practice of this invention, health data is preferably monitored on a substantially continuous, periodic, or quasi-periodic basis, meaning that data are taken or read and recorded periodically such as every few seconds, minutes, hours, days or longer. The periodic recording of data may extend for short periods such as a few minutes or days, or may extend for prolonged periods of time such as weeks, months or longer. The data is generally recorded seriatim or one after another. The data that is recorded may be varied from time-to-time depending on the analysis of data that is collected so as to collect data that may be more relevant to changes in a subject's primary elements. Data is recorded for doing low resolution analysis as well higher scale analyses. As used herein "health data" is used generically to mean all forms of data relating to health, including physiological data that include but are not limited to blood pressure, cardiac output, vascular activity, temperature, respiration, cardiac, abdominal, or breathing sounds, blood flow, hormonal concentration, enzyme and protein levels, genetic, proteomic, metabolomic, and molecular data, neural activity, electroencephalographic activity, and other electrical, mechanic, sonic, biochemical, and biophysical processes in the human body, other information related to human life, including demographic (age, gender), environmental (pollution, job conditions), and psychological data, life styles, exercise activities, etc.

In addition, this invention provides an easy-to-use system for structured and complete analysis and representation of data and its serial changes quantitatively for medical professionals. Structuring of the analysis is achieved by constructing the at least two, and preferably three, information scales that represent the most significant parameters at different level of detail. The multi-scale analysis and representation can be applied to all types of health data defined above. The values of the data obtained from individual patients can be compared with the average values obtained in a group or a population of patients to facilitate analysis of individual data and to determine the values that characterize groups of patients with similar characteristics and/or similar disorders.

A preferred embodiment of this invention further includes implementation of the multi-scale analysis. Specifically, this invention provides for the implementation of the multi-scale analysis on a distributed network of personal devices (which may include devices for registration and processing of electrocardiogram, electroencephalogram, blood pressure, cardiac output, temperature, respiration, vascular tone, blood glucose, and other biochemical, biophysical, biomechanical, hormonal, molecular, and genetic data) and centralized computers with a bi-directional communication between them. This distributed network allows: 1) uninterrupted data acquisition (continuous or discrete) anytime, anywhere, 2) fast transmission of the acquired information to the other computers on the network for processing and comparison with previously acquired serial data (including individual baseline data), 3) fast and accurate processing, analysis, and accurate detection of serial changes, 4) transmitting the results back to personal devices (held by the individuals and medical personnel) to inform them and adjust the monitoring thresholds.

On the network, the data and its processing may be distributed horizontally among the devices and computers according to the computational resources, time period of data acquisition, type(s) of a medical test(s), geographical location, professional and living environment. For example, one distributed personal network of devices and computers could be setup at home, a second network could be setup at a work place, a third network could be setup in a hospital, and a fourth one could be setup in a transportation system (such as a train or an airplane), so that all four networks are connected to each other and can exchange the information instantly. The personal devices may include devices for acquisition and analysis of electrocardiogram, electroencephalogram, electromyogram, blood pressure, impedance, vascular resistance, cardiac output, biochemical, genetic, proteomic, molecular, and other types of health and environmental data.

The advantages of the distributed processing include: 1) a higher computational power and speed of distributed parallel processing, which allow efficient implementation of such computationally expensive methods of artificial intelligence as neural networks, expert systems, and hybrid artificial intelligence systems, and other mathematical and statistical tools, and 2) fast exchange of information among the devices on the network as well as between different networks.

Low, intermediate and high-resolution scales are defined according to the corresponding software and hardware resources. A low-resolution (Scale I) represents a small number of the most important primary elements such as intervals between the heart beats, duration of PQ, QRS, and QT-intervals, amplitudes of P-, Q-, R-, S-, and T-waves. This real-time analysis is implemented in a portable device that requires minimum computational resources. The set of primary elements and their search criteria are adjusted for each physiological signal utilizing computational resources of intermediate or high-resolution levels. At the intermediate-resolution (Scale II), serial changes in each of the said elements are determined using a mathematical decomposition into series of orthogonal basis functions and their coefficients. This scale is implemented using a specialized processor or a computer organizer. At the high-resolution (Scale III), serial changes in all elements of the ECG and their combinations are extracted using orthogonal mathematical decomposition to provide complete information about the dynamics of the signal. This scale is implemented using a powerful processor, a network of computers or the Internet. Scale I may be implemented in a portable, pocket-size device, in which the signal is decomposed into a plurality of primary elements and parameters such as intervals between the heart beats, type of a cardiac complex, amplitudes and duration of P-, QRS, T-, and U-wave, QT-interval, amplitude of ST-segment. Scale I of the system provides the means for real-time electrocardiographic analysis by comparing the primary elements of ECG with reference values (individual thresholds) using the minimum computational resources. The reference values are programmed into the device based on normal values for the primary elements for the patient. Scale I includes means for adjustment of individual thresholds and criteria for rejection of noisy data. A detector of noise and error rejects the noisy data if the primary elements exceed physiologic range. Alternatively, modification of the primary elements and adjustment of their search criteria can be performed automatically at the higher-resolution Scale II or Scale III. In this case, the Scale I analysis is implemented using a programmable microprocessor that can be re-programmed at the higher-resolution scales to account for the individual characteristics of the physiological pattern and monitoring goals. Specific sets of primary elements can be used for patients with different cardiovascular abnormalities.

Scale I can be used in two modes: static mode and dynamic mode. The static mode is used for one-time ECG examination in which the newly acquired primary elements are compared with the default reference values. The dynamic mode is used for comparison of the newly acquired primary elements and waveforms with the primary elements and waveforms that were previously acquired from the same person. The shapes of QRS, T, and P-waves are compared using cross-correlation function. A small magnitude of the difference between the two measurements permits classifying them as substantially similar and keeping only one measurement in the memory.

Scale I provides sufficient information for standard, one-time, clinical ECG examination. The most significant primary elements may be represented as a color, symbol, or other easy-to-read encoding of indicators that make the results useful and understandable for a lay person and a medical professional. Each signal-indicator corresponds to a single primary element. In the static mode, the values of the indicators are preferably color-coded for a lay person into normal, moderately or severely abnormal. This representation constitutes a static screen. Alternatively, the indicators may be symbol-coded, N for normal and A for abnormal reading; or they may vibrate or produce a sound output for people with vision or hearing impairments. For a medical professional, the indicators provide exact, quantitative values of the primary elements. In the dynamic mode, the indicators are preferably symbol (or color)-coded into C for changed or U for unchanged. This representation constitutes a dynamic screen.

Intermediate-resolution Scale II allows viewing the ECG with automatically determined primary elements on a display and interactive editing of the set of primary elements and their search criteria. The editing can be performed by a user or a medical professional to modify the set of characteristic points or to adjust their search criteria, and can be performed either manually or automatically by the software. The individually adjusted search criteria can then be used to re-program the Scale I analysis as described earlier.

Scale II allows accurate comparison of serial ECGs and detection of small serial changes that may be unexposed by visual inspection of the signals. This scale requires higher computational resources than Scale I and can be implemented in a specialized processor, computer organizer or a personal computer. These computational resources also allow manual entering text information about the patient into the database and specific instructions regarding adjustment of time windows, threshold values, and other variables. To perform the Scale II analysis, the primary elements from serial ECGs are stored into a database to construct the time series for each primary element. The series is decomposed into a few most significant basis functions and coefficients using Principal Component Analysis (PCA) or any other orthogonal set of basis functions. The newly acquired values of the primary elements are compared with the series of the previously obtained values. Furthermore, the changes in the series of PCA coefficients are analyzed to detect small cumulative changes in the dynamics of the series that indicate instability in the cardiac electrical activity.

High-resolution Scale III is used to analyze individual and combined changes in the primary elements; at this scale, the number of the primary variables is increased to include the entire waveform of the cardiac complexes. This allows the most sensitive and accurate detection of the small changes in the individual electrocardiographic pattern. The same PCA approach is used at this scale to expose small serial changes in the ECG recordings. Scale III requires higher computational resources compared to Scale I and Scale II; it may be implemented in a powerful processing unit such as a personal or specialized computer or a distributed network of computers or the Internet.

This invention can be used for one-time examinations by patients, medical professionals, paramedics and lay public, and for dynamic assessment of changes in cardiac electrical activity. The information can be transmitted to an external computer system or a network of computers. For a lay person, the system may also include a database explaining significance of the changes in each primary element and providing simple recommendations about the measures that has to be taken if the readings of the indicators become abnormal. These may include complete cessation of physical activity, contacting a medical professional, taking a medication, etc. More detailed recommendations might be provided for patients who have specific abnormalities or medications. These patients might require special monitoring or individual adjustment of their primary elements. For example, specific monitoring the duration of QT-interval is important in patients taking antiarrhythmic drugs that prolong QT-interval.

The system can be used as:
Hospital or medical center information management;
Information management for ambulatory patients;
Information management for community health program;
Information management for corporate health program;
Self-awareness and health advice system;
Information management for patients with implantable devices;
Medical decision support system for medical professionals implemented on a personal computer, a cell phone, a smart phone, or a personal digital assistant (PDA);
Information management or decision support system that includes personalized analysis of serial data and medical knowledge contained in medical literature and on the Internet;
Personalized advice system implemented on a personal computer, a cell phone, a smart phone, or a personal digital assistant (PDA);
First-aid health-data analyzer for emergency units, paramedics, and medical personnel;
Health data analyzer for a routine medical examination;
A personal one-time or serial data analyzer with storage of individual historic data, adaptive adjustment of individual thresholds and assessment of changes in individual heath pattern;
A one-time or serial health-data analyzer for a group of people, a family or a patient group, with storage of individual historic data for each person, adjustment of individual thresholds and assessment of changes in individual health patterns;
Event-monitoring device including patient-detected events;
Bedside monitoring;
Bedside or ambulatory monitoring providing intelligent alarms to medical professionals when appropriate;
At least one of arrhythmia, stress-test, ischemia, ST-segment, and T-wave alternans monitoring;
Pacemaker and other implantable device checking, bi-directional or uni-directional communication, programming, and control;
Evaluation of the treatment efficacy, side effects and progression of the disease.

Accordingly, an object of this invention is to provide a system for analyzing ECG signals at least at two levels of detail or resolution. Both levels of resolution are presented in simple representation that can be understood by lay persons, as well as medical professionals.

A further object of this invention is to provide an ECG analyzing system that includes a monitoring device for receiving and analyzing ECG signals and which includes means for communicating with an external computer to which the ECG signals can be forwarded for more complex analysis. The monitoring device can be reprogrammed by the external computer to select the primary elements of the ECG signals that are unstable or abnormal. The low level analysis performed by the monitoring device is thus focused on the critical primary elements for that patient.

The system of the present invention can be used for management and analysis of electronic health (medical) records and information, analysis and management of biometric data, or information management of other types of healthcare data.

The system of the present invention provides instant access to information from a variety of distributed sources to reduce costs, improve quality of patient care and optimize decision making. For example, the system can be used to provide a real-time view of inhospital patient distribution and operations structure in different departments and at different stages of the treatment process, from admission to discharge, or in the Emergency Room. The system can capture and integrate monitoring of vital signs, biometrical data, capture and integrate text, images, technical information related to device functioning and instrumentation status. The system can also provide an intelligent, tailored representation for different types of users and different points of care. For example, it can improve information sharing among the healthcare providers, including physicians, nurses, technicians, clerks, and others. The system of the present invention can also facilitate analysis, management, and optimization of information processing from the traditional departmental systems—e.g., legacy systems (Nursing, Pharmacy, LIS, RIS, PAS, by creating integrated database, applying intelligent analysis and optimizing diagnosis and treatment, including diagnostic and treatment plans and providing intelligent alarms and alerts to support and optimize clinical decision making.

The system of the present invention can collect real-time physiological and health data from a variety of sensors including vital sign monitors, ventilators, infusion pumps. It can also support a wide range of physiologic sensors from a variety of manufacturers. The system can also automatically re-configure itself to accept and recognize new data from physiological sensors whenever a new sensor is plugged into the system. It is also possible to enter new data into the system using an integrated barcode scanning or RFID tag or MEMS tag or other types of automatic entry of information at the bedside in a real time. The system of the present invention can also adapt, compare and merge new information with the data that already exist in the system.

Because the information flow between different levels/units of the system is bi-directional, the system supports and optimizes seamless exchange of data coming from different diagnostic and treatment modalities, such as patient information from hospital data repositories (e.g., Laboratory, Medication, Admission/Discharge/Transfer and others) and intelligently alert the clinician to potential problems.

The system can also have multiple displays, terminals, including wireless connections with personal handheld devices (PDA, Smart Phones, Cell phones, computers, and computer tablets). Using these displays, users can simultaneously receive different modes of information, such as physiological signal information (vital signs, ECG, blood pressure, cardiac output), real-time intelligent alerts, prescription dispensing, drug interaction, dynamical report, individual patient dynamics, and serial comparison of individual patient's data, etc.

For example, an acute ischemic syndrome (AIS) can be confirmed by measurements of the level of cardiac enzymes (troponins). Since the level of enzymes can be estimated only in a hospital, this information is usually unavailable when the subject is admitted to the emergency room. In the absence of this information, medical decision is made on the analysis of clinical and electrocardiographic signs of ischemia. Yet, this information is incomplete. Thus, the information completeness is estimated relative to the total, theoretically possible, information about a disease state (which is equal to 1), so that the sum of information content (probability estimates, or uncertainty) of all diagnostic tests is equal to 1. The information contained in each test is equal to a number between 0 and 1. At each scale the information completeness (probability of each disease state) can be estimated relative to the complete information (reference) for this disease state. Similarly, the information completeness is also estimated for all scales, relative to the complete, theoretically possible information in all scales.

The probability or information completeness can be represented by the probability transition matrix of a Markov chain, Bayesian probability, probabilistic neural network, or some other non-probabilistic matrices and methods.

Traditionally, the term "multiscale analysis" or "multi-resolution analysis" refers to either (1) a spatial multiscale analysis (distributing analysis of complex structures or processes that span different spatial scales, for example, molecular-cellular-organ-body scales of biological processes into several spatial scales), or (2) a temporal multiscale analysis (distributing analysis of complex, dynamic processes that involve several different time-scales). The term multiscale analysis used herein refers to the temporal multiscale analysis adapted to serial (longitudinal) data or a combination of temporal and structural multiscale analysis adapted to serial (longitudinal) data (because serial images, image information, and other data spanning different spatial scales can be also included in the analysis). Note that the traditional temporal multiscale analysis refers to an application of a mathematical formula or function (for example, a wavelet function or a nonlinear function, such as entropy), to different time-scales by varying a time-window parameter (i.e. using a mathematical translation or dilation of a function). A detailed description of a multiscale wavelet analysis can be found in The Statistician (2000) 49, Part 1, pp. 1-29 (Abramovich F, Bailey T C, Sapatinas T. Wavelet analysis and its statistical applications.). A description of a multiscale entropy analysis can be found in Physical Review E 71, 2005, pp. 0219061-02190618 (Costa, M, Goldberger A L, Peng, C.-K. Multiscale entropy analysis of biological signals). In this approach, the fundamental mathematical function remains unchanged at all time scales, but the scaling parameters change. Our multiscale approach, presented herein and in our previous applications (application Ser. No. 10/816,638, filed Apr. 2, 2004, which is a continuation-in-part of application Ser. No. 10/124,651, filed Apr. 17, 2002, now U.S. Pat. No. 6,925,324, which was a continuation-in-part of application Ser. No. 09/583,668, filed May 30, 2000, now U.S. Pat. No. 6,389,308), incorporated herein by reference, is different from the traditional methods for multiscale analysis described above (in some respects, it can be viewed as a non-trivial generalization of the traditional multiscale and multi-resolution approaches). It allows 1) usage of different mathematical, pattern-recognition, statistical, probabilistic, artificial-intelligence functions/models/estimates/approximations at different time scales, 2) usage of a single time-point (snapshot) compared against reference values at the $1^{st}$ scale of analysis (this snapshot analysis can be performed one-time, periodically, quasi-periodically, or continuously) and multiple time-points (serial data) at the higher-scales of analysis, 3) usage of composite functions and estimates obtained by combining different parameters and time-scales at higher-level analytical scales, 4) bi-directional exchange of information between different scales to improve the analysis. Using recently introduced terminology, our multiscale analysis approach can also be viewed as a non-trivial extension, improvement, and generalization of a recursive projection method (Shroff G M, Keller H B. (1993) *SIAM J. Numer. Anal.* 30, 1099-1120) that can be also adapted for "equation-free modeling" (Theodoropoulos C, Qian Y-H, Kevrekidis I G. *PNAS* (2000) 97, 9840-9843) of multiscale, complex processes.

FIG. 4 shows an example of time-varying physiological data recorded during sleep in a middle-aged subject with a variable breathing rate. This figure demonstrates the difficulties of serial analysis of such time-varying data, with multiple, complex relationships between the signals and illustrates the advantages of using PBFs for improving serial analysis, detection and classification of physiological waveforms. FIG. 4 shows simultaneously recorded electrocardiogram, breathing and physical movements (changes in body position). Note that breathing and changes in body position cause concomitant changes in the ECG waveforms. Specifically, respiratory movements are associated with changes in the heart orientation vector causing changes in the amplitude of the R-wave and other ECG waves. Similarly, changes in body position also cause changes in the heart orientation relative to the ECG recording electrodes on the body surface, resulting in varying amplitudes of the ECG S and T waves and the segments between P and Q waves, T and P waves, S and T waves (FIG. 5).

Thus, constructing a separate PBF, representing the time series of ECG waveforms and respiratory movements for each body position, as described above, and using it as a personalized, fine-tuned template for a specific body position, will allow more accurate detection and classification of the ECG waveforms (P, QRS, ST, T and U-waves) and tracking serial changes in the ECG waves' amplitudes, durations and intervals (e.g., QT-interval, RT-interval, T-wave alternans, and nonalternating repolarization instability). This will also allow more accurate classification of the sources of ECG changes, including those caused by respiration, physical movements and changes in body position. By comparing newly acquired data with such body-position-specific, fine-tuned PBFs, one can also track the dynamics of: i) breathing (including changes in the frequency, irregularity, amplitude and duration of pauses), ii) body position and iii) physical movements (increased restlessness or loss of movements, which should provide an indication of a serious health problem such as loss of consciousness). Using PBFs as precise, fine-tuned references also improves the accuracy of remote monitoring (in elderly people at home, in seriously ill patients in a hospital, or in infants) without the need for surveillance by a video-camera or a human attendant, which may be unavailable or inappropriate. Other examples of PBFs include the times series of blood pressure waves, cardiac output and intrathoracic fluid (impedance) obtained during different physiological states (e.g., sleep, exercise, rest, food intake or mental stress).

FIG. 6 shows an example of the 3-variable PBFs obtained during nighttime (black dots) and daytime (grey dots) periods from a 24-hour ambulatory Holter ECG recording in a middle-aged person. The variables are beat-to-beat changes in heart rate (i.e., the intervals between consecutive electrocardiographic R-waves), and two Karhunen-Loeve (KL) coefficients obtained by the KL-decomposition of the time series of electrocardiographic STT-complexes, as disclosed in the Shusterman patents listed above. Note the clear difference between the nighttime and daytime PBFs. Similarly, FIG. 7 shows an example of 2-variable PBFs obtained in the same person during night and day periods. The two variables are electrocardiographic RR-intervals and QT-intervals. In this 2-variable state space, the nighttime and daytime patterns are also separated, although the separation is less clear than in the 3-variable space shown in FIG. 6. Thus, these PBFs can be used as personalized templates or references for more accurate tracking of serial changes during daytime and nighttime periods, respectively. The changes can be estimated by comparing the corresponding patterns of individual dynamics over consecutive time intervals using time-domain, frequency-domain method, cross-correlation, cross-coherence, Karhunen-Loeve transform, Fourier transform, linear regression, non-linear regression and other methods disclosed in the Shusterman patents listed above.

PBFs can also be used for identifying the indvidual's type of physiological activity (i.e. "reverse engineering" of the activity at the time of the recording) by comparing the newly recorded patterns with a set (library) of personalized PBFs recorded during various physiological activities. Therefore, PBFs can be also used for determining the time of the recorded data from the pattern of physiological activity.

In addition, PBFs can also be used for identifying a sequence of consecutive physiological activities over longer time intervals (i.e., multi-scale analysis over multiple time scales) by comparing the patterns of newly recorded data with a sequence of PBFs. For example, a Holter, telemetry or implantable ECG recording obtained over 24 hours can be compared with a library of shorter PBFs to identify a sequence of physiological activities performed during 24 hours or longer time intervals.

Multi-scale PBFs can also be constructed using a sequence of shorter PBFs to represent 24-hour, 48-hour or seasonal patterns of physiological dynamics. The PBFs can be adjusted for age, gender, weight, medical history, occupation, genetic, biochemical and other biological and environmental factors.

Fusion of Templates Representing Different Signals

As shown in FIG. 6, the PBFs can incorporate several different time series, thus representing information fusion of different data types. Such a fusion allows better identification of interactions between different data types. For example, respiration, physical movements, changes in body position, heart rate and vascular activity can affect the amplitude of the electrocardiographic T-wave and ST-segment, which needs to be taken into account to avoid classification errors. In particular, changes in body position can mimic ischemic changes in the ST-segment, and changes/instabilities in breathing frequency and heart rate may mimic changes in the magnitude of T-wave alternans.

A Library of an Individual's PBFs

Each individual's sequence of physiological activities and health dynamics can be completely described by a library of individual PBFs, which represent physiological data associated with various physiological activities and the transitions between them. For example, this library may contain PBFs of serial data (ECG, heart rate, blood pressure, cardiac output) during REM and Non-REM sleep, transition from sleep to wakefulness, morning exercises, and other physiological activities.

It is well known that blood pressure, ECG waveforms, heart rate and cardiac output exhibit day-to-day, circadian and seasonal variations. A library of individual PBFs, associated with specific physiological activities, can improve the accuracy of tracking physiological dynamics compared with currently available methods. For example, comparing an individual's recent data obtained during morning exercises with the same individual's historical data also obtained during morning exercises will expose subtle or gradual changes, which cannot be detected without such an accurate PBF-based reference.

One particularly important property of a PBF is its accurate description of the physiological patterns arising during the transition from one physiological activity to another. These high-risk periods often lead to physiological instabilities and complications. For example, a transition from sleep to wakefulness during morning hours has been associated with heightened risk of myocardial infarction, sudden death and ventricular tachyarrhythmias. This period is also associated with proarrhythmic electrical instabilities in the heart manifested by T-wave alternans.

Markov models and hidden Markov models are particularly suited for describing such physiological transitions in terms of probabilities, using the transition probability matrices, as shown in the Shusterman patents listed above. These matrices describe the probabilities of transition from one state to other states (for example, from sleep to wakefulness). In the hidden Markov models (HMM), the states can be hidden or unknown, and the model can be based on the statistics of observations (i.e., physiological data patterns, PBFs) only.

For example, a left-right HMM can be constructed in such a way that the probability of a change in the physiological state is associated with a set of characteristics $\Theta=\{\pi,A,B\}$, where $\pi$ is a prior probability (i.e. the probability that the subject is initially in a certain physiological state, physiological activity, state of health, or state of disease), A is a transition matrix of probabilities of going from one physiological state to another (e.g., from sleep to wakefulness, from health to a disease, from one stage of heart failure to another, from uncomplicated chronic disease to a complication), and B is a matrix of emission probabilities (also referred to as the observation matrix) that describe the likelihood of observing a certain PBF or its characteristics (e.g., those shown in FIG. 6) when the subject is in a certain physiological activity/state (for example, sleep). The matrix B may contain probability density functions, vectors, or mixtures of functions. The above matrices can also contain some parameterizations derived from the PBFs, such as mean/median values and variances or ranges. The observation matrix may also include some confidence measures that describe confidence that the newly acquired data are accurate. This matrix may also contain probability density functions for different distributions, including exponential, Poisson, Gaussian or multivariate Gaussian mixtures models (C.A. Glasbey. Nonlinear autoregressive time series with multivariate Gaussian mixtures as marginal distributions. 2001, Applied Statistics, 50, 143-154; 0. Boldea, J. R. Magnus. Maximum Likelihood Estimation of the Multivariate Normal Mixture Model. Journal of the American Statistical Association. Journal of the American Statistical Association. Dec. 1, 2009, 104(488): 1539-1549.) derived from a covariance matrix or an artificial neural network. These models may be trained using the Expectation-Maximization algorithm (EM), the Baum-Welch algorithm (a special case of EM algorithm) or the Baldi-Chauvin algorithm. In addition to linear optimization procedures, a neural net may also be trained by a non-linear optimization procedure, such as Scaled Conjugate Gradients and its extensions for multi-step time-series forecasting (Falas, T.; Stafylopatis, A. Temporal differences learning with the scaled conjugate gradient algorithm., 2002. ICONIP '02. Proceedings of the 9th International Conference on Neural Information Processing, 2002, vol. 5, p. 2625-2629. ISBN: 981-04-7524-1). The observation vectors may be also obtained using the coefficients of a linear orthogonal decomposition and their derivatives, as described in the Shusterman patents cited above. Examples of linear transforms include the Karhunen-Loeve transform, Fourier transform and wavelet transform.

The joint likelihood of a sequence of PBFs (i.e. the likelihood of observing a particular sequence of PBFs, X, along a certain path or sequence of changes in the physiological activities/states, Q) can be computed using the Bayes conditional probability:

$$P(X, Q \mid \Theta) = P(X \mid Q, \Theta) \cdot P(Q \mid \Theta) \quad (1)$$

$$\text{where} \quad (2)$$

$$P(X \mid Q, \Theta) = \prod_{n=1}^{N} P(x_n \mid q_n, \Theta) = b_{q_1,x_1} \cdot b_{q_2,x_2} \cdots b_{q_N,x_N}$$

Formula (2) represents the likelihood of a certain sequence of PBFs, X, along a certain path of physiological states/activities, Q; $b_{q_N,x_N}$ are emission probabilities that describe the likelihood of observing a certain PBF, $x_n$, or its characteristics (e.g., those shown in FIG. 6) when the subject is in a certain physiological activity/state, $q_n$, (for example, sleep). Next, probability of a sequence of physiological states given a set of parameters $\Theta$ is equal to a product of transition probabilities, $\alpha_{q_n,q_{n+1}}$ from physiological state $q_n$ to physiological state $q_{n+1}$, along a path and a prior probability, $\pi$, (i.e. the probability that the subject is initially in a certain physiological state, $q_1$, physiological activity, state of health, or state of disease):

$$P(Q \mid \Theta) = \pi_{q_1} \cdot \prod_{n=1}^{N-1} a_{q_n,q_{n+1}} = \pi_{q_1} \cdot a_{q_1,q_2} \cdot a_{q_2,q_3} \cdots a_{q_{N-1},q_N} \quad (3)$$

Using formulas (1)-(3), one can compute the likelihood of an observed sequence of PBFs for each sequence or path of physiological states/activities or disease states, Q. Then, one can determine the sequence or path of changes in the physiological state associated with the greatest likelihood, and this will be the most likely sequence of changes in the physiological states. To reduce the amount of computations, this analysis can be implemented in software using a recursive Viterbi algorithm, or other recursive, forward-backward computer algorithms. To represent (visualize) the dynamic changes in the probabilities of different physiological states (or disease states) for a user, one can use Trellis diagrams.

To determine the most probable HMM for a given sequence of PBFs or their characteristics, one can compute first, for each HMM, the probability of the most likely path (sequence) of changes in the physiological/disease state as described above (see (1)-(3)). Then, an HMM that has the greatest probability of the most likely path would be the most probable HMM model.

One can also compute a normalized probability of an HMM, by normalizing the probability of the most likely path (sequence) of changes in the physiological/disease state for each HMM, by a sum of the joint likelihoods for the particular sequence of PBFs and all possible physiological activities/states or disease states, Q, allowed by the HMM as follows:

$$P(X \mid \Theta) = \sum_{allQ} P(X, Q \mid \Theta) \quad (4)$$

Equation (4) also provides a way to compute the probability of observing a certain sequence of PBFs for a given HMM (over all physiological/disease states). Using formula (4) for different HMMs, allows one to determine a model (among several models), which gives the greatest probability of observing a particular sequence of PBFs.

It is also possible to construct a second-order Markov model in which the probability of a certain physiological or disease state will depend on 2 previous states (unlike in the $1^{st}$ order Markov model, where the probability of a state depends only on the previous state). Obviously, the idea of the order of the model can be generalized to any other number n=3, 4, 5 ... N.

It is also possible to "train" HMM on data with known properties to determine the optimal set of parameters ($\Theta=\{\pi, A, B\}$ defined above) that maximize the accuracy of the model with respect to a physiological/disease state or sequence of states associated with particular PBFs. The "training" goal could be determined according to the specifics of a particular healthcare application, treatment goals, cost/benefit functions and ratios and other optimization methods.

The Markov models and hidden Markov models, as well as other Bayesian, probabilistic models/networks, can be used for dynamic analysis of any physiological state or activity or disease state or health data using PBFs in any population or individual. PBFs with these analytical tools can be also used for tracking the probabilities of presence/changes in several alternative or non-alternative (coexisting) physiological states/diseases (differential diagnosis).

Development, Training and Testing of PBFs

Initially, PBFs can be obtained by collecting individual's serial data during specific physiological activities (sleep, wakefulness, exercise, rest) and extracting typical serial patterns using, for example, a linear orthogonal decomposition (Karhunen-Loeve, Fourier, Laplace or wavelet transform) of the covariance matrix, as shown in Shusterman patents. The resulting coefficients, eigenvectors and eigenvalues contain complete information about the structure of the serial patterns. The magnitude of each eigenvalue is associated with the magnitude of the information (variance) that the corresponding eigenvector represents. Thus, selecting different combinations of the eigenvectors and their coefficients allows representation of different (orthogonal) properties or information contained in the serial patterns. Similarly, wavelet coefficients or Fourier transform coefficients can be used to represent serial patterns as well. The probability that a subject is in a particular physiological state, given a specific PBF (observation) and the probability of transitions from one physiological state to another one can be represented using a hidden Markov model, as described above. Training and testing can be performed using standard procedures for hidden Markov models. Initially, in the absence of information regarding individual's PBFs or associated physiological activities, the training of the model can be started using default, population-derived PBFs (patterns). They can be later adjusted or "tailored" to an individual's pattern using Markov models or other statistical methods. Alternatively, the information regarding specific physiological activities can be manually entered or constrained by a human operator at any stage of the model training. The PBFs can be also adjusted for the circadian or seasonal variations and other factors, including age, sex, weight, disease, medical history and other covariates (for example, blood pressure, cardiac output, pulmonary pressure, intra-thoracic fluid volume, heart rate and blood count).

Segmentation, Detection of Unstable or Transitory Periods and Time Stamping

Segmenting physiological data recorded, for example, using implantable devices, telemetry or noninvasive monitoring, into periods of different physiological activities (e.g., sleep, wakefulness, rest, exercise, etc.) represents a major challenge. For example, the severity of chronic heart disease and its progression can be evaluated based on tolerance (i.e., physiological response) to physical activities. Tracking the level of activity is, therefore, critically important in such patients. PBFs can be used to provide accurate segmentation of data into the segments corresponding to different physiological states, including different levels of physical activity. The initial start times for a segment may be selected from: i) fiducial points (e.g., electrocardiographic R-wave), ii) fusion of several signals (for example, the time point of the electrocardiographic R-wave that coincides with the peak of the inhaling phase of a breathing cycle), iii) a known onset time of a particular physical activity (exercise), mental activity (mental stress) or physiological process (sleep, wakefulness, food intake, etc.).

As described above, the transition from one PBF to another PBF (i.e., from one physiological state or activity to another) identifies transitional periods, which are often associated with a heightened risk of complications or instabilities. For example, myocardial infarction, ventricular tachyarrhythmias and sudden death all happen during morning hours (i.e., during the transition from the period of sleep to wakefulness). Similarly, the transitions from rest to exercises, to higher-intensity exercises, and back to rest are also associated with heightened risk of cardiovascular complications. Therefore, it is important to examine not only the stationary PBFs, but the duration of the transitional periods, presence of random, non-periodic variations (i.e., noise), their structure (e.g. white noise, brown noise), presences of fractals and chaos.

For example, during the transition from rest to physical activity, heart rate increases and the electrocardiographic QT-intervals shorten. Using the corresponding "transitional" PBF, it is possible to estimate/model the exact relationship between the heart rate (i.e., RR-intervals) and QT-intervals. This can be accomplished by using the coefficients of a linear orthogonal decomposition of the corresponding covariance matrix, as shown in Shusterman patents listed above, or wavelet coefficients, a combination of exponential functions, or other methods of linear regression, pattern recognition and neural networks. Subtracting the slow trends from the time series of QT-intervals (determined by changes in heart rate) would leave the residual QT-interval variability, whose fine temporal structure could be studied using several methods. These include: i) the correspondence (cross-correlation or cross-coherence) between the beat-to-beat QT and RR-interval variabilities, and ii) the fine structure (randomness, symmetry, curtosis, flatness, etc.) of such distributions. These features of the QT-interval (or T-wave amplitude) residual beat-to-beat variability could reflect the features of the system dysadaptation, including the direction/component of maximal dysadaptation and links to the underlying electrophysiological mechanisms. This type of analysis could be useful for clinical studies of new pharmacological agents and their effects on cardiac electrical stability. This might also be useful for studying the patterns of QT-interval dysadaptation/instabilities associated with ischemia, high risk of sudden death, specific patterns of autonomic activity, exercise, physical or mental stress.

Assuming that the short-term, beat-to-beat RR-interval variability has random components and taking into account the fact that the QT-interval adaptation is relatively slow, the short-term RR/QT interval system is equivalent to the classical input-output system in which the input is a random noise. Therefore, taking the Fourier transform of the QT-interval (or T-wave amplitude) variability would characterize the system output. A higher-dimensional Fourier transform can be applied to characterize the system in a higher-dimensional space representing different time scales, different memory functions or different histories of the RR-interval trends (hysteresis). One example is a space comprised from respiratory and circadian variations in the QT-intervals.

Estimating the difference (e.g., Euclidean or Mahalanobis distance) between the newly acquired data and corresponding PBFs facilitates quantification of data irregularities and disturbances. FIG. 8 shows increased randomness and abrupt disturbances in the time series of electrocardiographic T waves during morning hours quantified as the distance (difference) between the time series of T-wave amplitudes and the $1^{st}$ and $2^{nd}$ Karhunen-Loeve coefficients of the corresponding time series. These Karhunen-Loeve coefficients are associated with the eigenvectors representing most of the energy (variance) of the signal; therefore, these coefficients can be considered as PBFs, representing characteristic features/patterns of the data. An increase in the signal irregularity, abrupt oscillations, randomness and more generally, a shift in the dominant frequency content to higher-frequency, irregular oscillations can be a marker of system instability and impending complications.

Furthermore, estimating the difference (e.g., Euclidean or Mahalanobis distance) between two consecutive PBFs (e.g., nighttime and daytime series of heart rate, T-wave amplitudes or QT-intervals) quantifies an individual's characteristics (e.g., range, rate and duration) of the transition from one physiological state to another. These characteristics can be used to quantify cardiovascular fitness and autonomic nervous system activity, in addition to the traditional indices of autonomic activity.

Thus, the distance between the newly acquired data and respective physiological basis function can quantify signal randomness, irregularity, and shift in the dominant frequency. In addition, the distance between the physiological basis function representing different time periods can quantify autonomic nervous system activity, baroreflex, fitness, health, disease progression, risk of sudden death, risk of death, treatment effects, risk of complications and side effects.

If the structure/pattern of physiological noise in the QT-interval or T-wave amplitude variability is known, then it can be used to differentiate physiological from non-physiological sources of noise. Similarly, if the structure of non-physiological noise is known a priori (for example, the electromagnetic interference, low sampling rate, or signal resolution), then it can be also used to differentiate physiological from non-physiological noise. Therefore, the knowledge of the total noise and at least one of physiological and non-physiological noises, allows one to determine the remaining component.

This approach can be useful for identifying sub-clinical side-effects of new pharmacological agents at the earliest stages of clinical trials. It is also possible that the total magnitude of the residual physiological noise contains prognostic information, which needs to be examined in clinical studies.

The hidden Markov models, representing transitions between physiological states using the transition probability matrices, were described above. In addition, specific "transitional" PBFs can be defined to represent specific transitional periods (e.g., morning hours, transition from rest to exercise and back to rest). Such specific transitional PBFs allow tracking of serial, day-to-day changes that occur during the specific transitional period over extended periods of time. For example, a deviation in the pattern of ECG data acquired during morning hours from the corresponding "morning" PBF constructed in the same person can identify a disturbance or instability. Such a deviation can be estimated using cross-correlation between the newly acquired data and the corresponding PBF. Alternatively, the newly acquired data and PBFs can be compared using the time series of their coefficients obtained by applying a linear orthogonal or non-orthogonal decomposition or other typical characteristics obtained from the covariance matrix of the time series. Significant disturbances in the time series can be quantified using the thresholds of 2 or 3 standard deviations from the mean value. Other methods include cross-coherence, Euclidean or Mahalanobis distances, regression and discriminant analysis, and other mathematical, statistical, modeling, pattern-recognition, artificial-intelligence and time-series analysis methods described in Shusterman patents listed above.

The PBFs also allow accurate segmentation of the time series into a sequence of physiological states and identification of the minimal duration of each state or a sequence of states. The minimal duration of a sequence of states can be determined as a sum of the minimal durations of all PBFs in the respective sequence. A transition from one PBF (state) to another can only occur after the minimal duration of the current state has been exceeded. Otherwise, a decision is made that the system remains in its current state. One can also determine the mean, maximum, median, mode and other statistical properties and statistical distributions of physiological states/activities from the properties of their respective PBFs.

Subject Identification (ID) and Fingerprinting PBF (State)

Another application of PBFs is subject identification for security and other purposes in the workspace, military, police, healthcare and other settings. This includes individual's identification (physiological profiling or fingerprinting) to allow access to a secure work area, car, computer or house.

PBFs can also be used for subject ID in clinical trials to ensure accurate data analysis. Subject IDs are often unavailable, lost or incorrect. Other applications of subject ID include remote and home monitoring of disabled and elderly people with impaired communication skills, in-hospital monitoring of critically ill patients, post-operative monitoring, and monitoring in the emergency setting and other healthcare settings.

Applications in Disease Control, Treatment and Stress Management

Since PBFs allow an accurate identification of an individual's sequence of physiological activities/states, these functions can be used for patient management, disease control and treatment, as well as stress management. Using PBFs as personalized templates or references facilitates an accurate quantification of treatment/disease progress, transition from one disease stage (e.g., heart failure stage) to another. This also facilitates early detection of disturbances or instabilities (e.g., deviation from an individual's respective PBF by more than 2 or 3 standard deviations), which can prompt a warning for a patient to reduce or stop all physical activity, take a medication, call a healthcare provider, or send this information to a healthcare practitioner.

Similarly, an extreme deviation from an individual's historical PBF during psychological stress can be used for biofeedback or serve as an indicator of a high stress level and the need for stress management or medication.

In addition, the knowledge of an individual's sequence of PBFs can be used to identify or predict (for example, using Kalman filter, analytic continuation or some other predictive method described in the Shusterman patents listed above), the time of high-risk periods associated with transitions or instabilities, during which an individual might be particularly vulnerable to stressors and stimuli and need to avoid excessive physical, occupational, environmental or mental stress. Such information could be provided to the individual or to the healthcare professional for designing an optimal patient management strategy. Furthermore, the knowledge of an individual's sequence of PBFs can serve as a guide for designing an optimal training regime or work schedule. It can also serve for guiding the times and doses of medication intake, to optimize treatment and disease control. It can also guide scheduling the time/date of elective procedures or surgery, to avoid high-risk, transitional periods and optimize recovery.

Although most examples herein are related to the field of medical monitoring, other applications of this invention are obvious for those skilled in the art.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Figure 1:
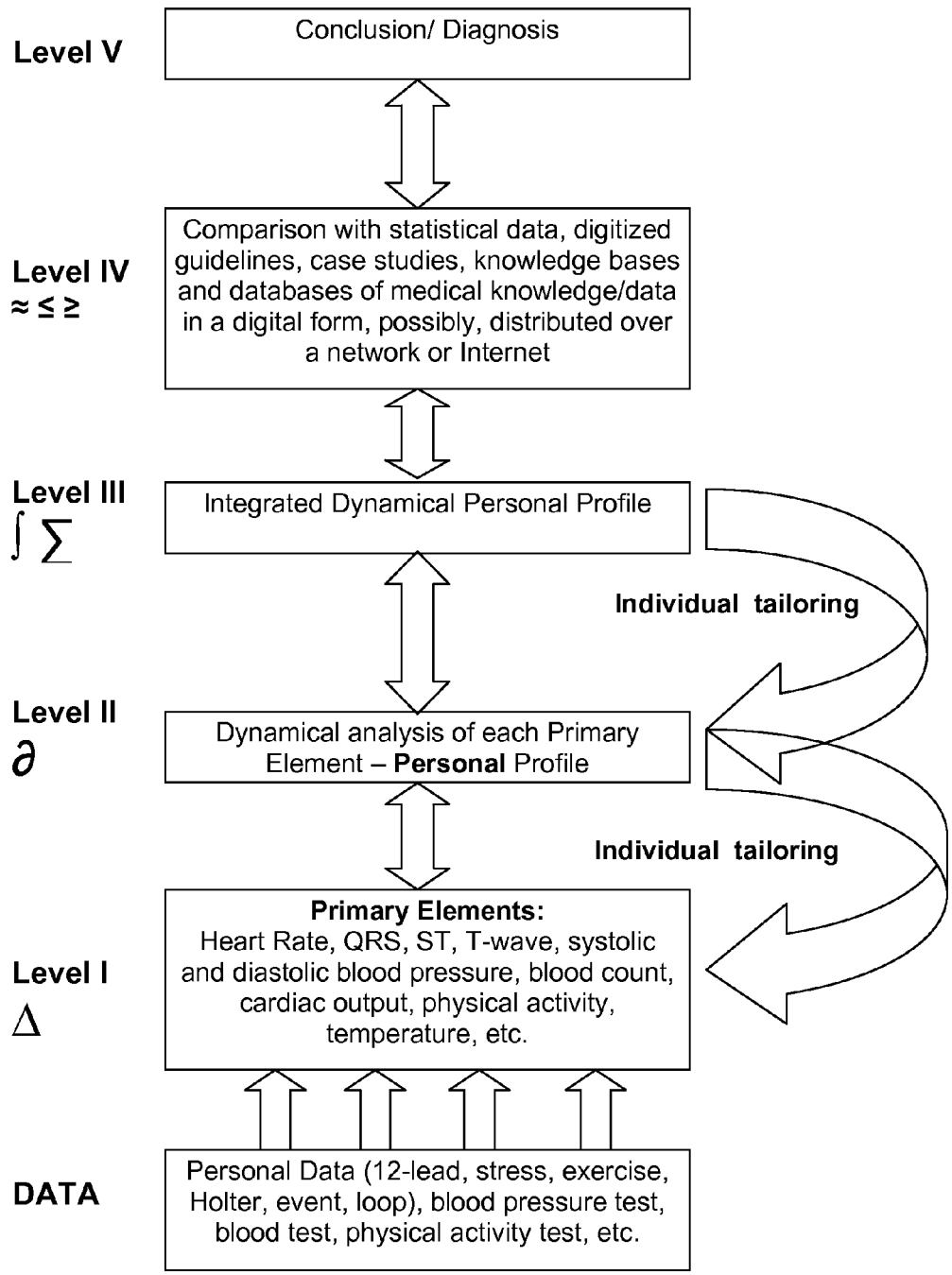
FIG. 1 is a flow chart of multi-scale analysis and representation of health data in accordance with this invention.
Figure 2:
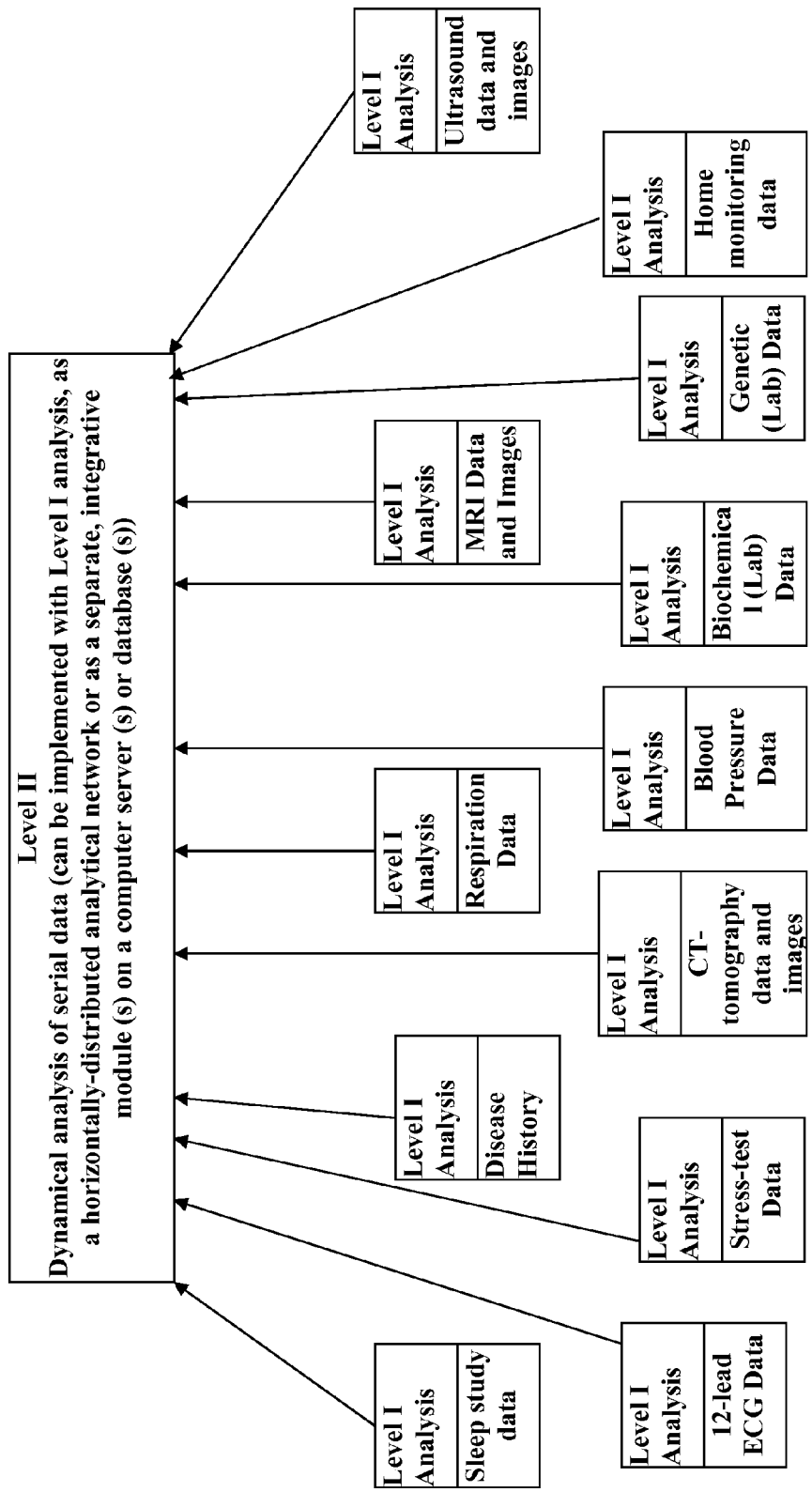
FIG. 2 is a flow chart showing horizontally and vertically distributed multiscale analysis and representation of health data in Levels I and II (with horizontally distributed Level I analysis).
Figure 3:
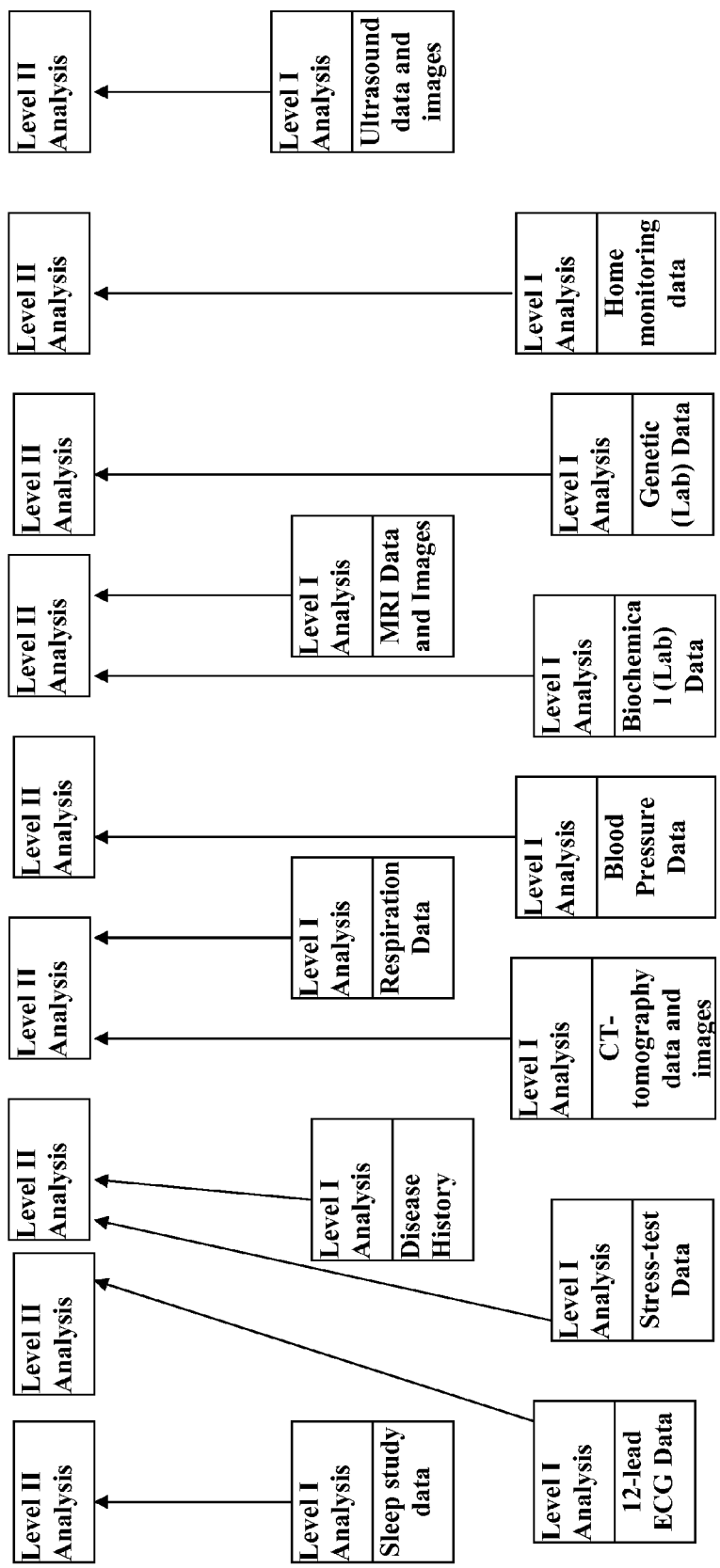
FIG. 3 is a flow chart showing horizontally and vertically distributed multiscale analysis and representation of health data in Levels I and II (with horizontally distributed Level I and II analyses).
Figure 4:
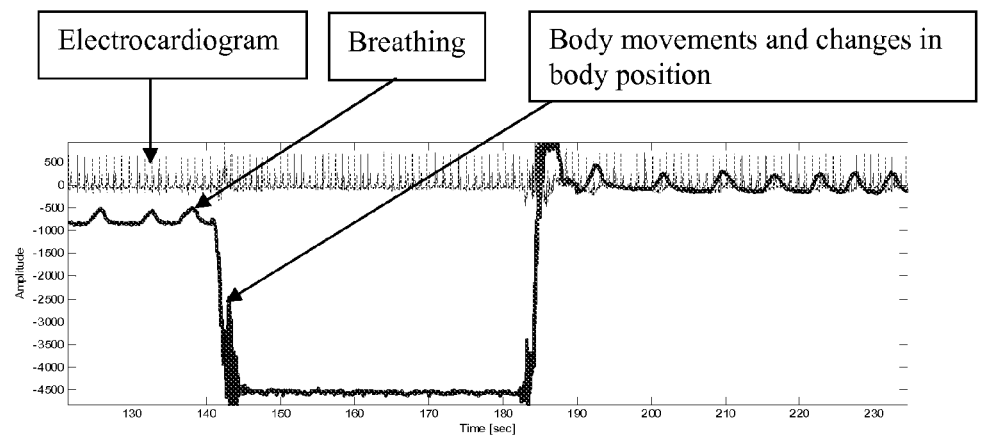
FIG. 4 plots physiological data, including electrocardiogram, breathing and body movements, recorded simultaneously during approximately 100 seconds in a middle-aged male with an irregular breathing pattern.
Figure 5:
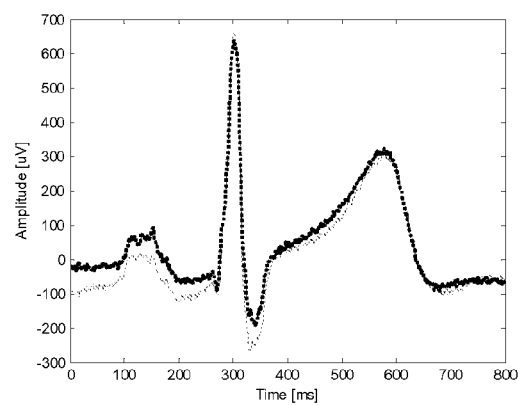
FIG. 5 plots changes in the amplitudes of electrocardiographic waveforms (S and T waves) caused by changes in the subject's body position and associated changes in the orientation of the heart vector relative to the recording electrodes.

FIG. 4 is an example of three physiological signals, electrocardiogram, breathing and body movements, recorded simultaneously during approximately 100 seconds, in a middle-aged male with a variable breathing rate. Such irregular respiratory movements that occur during the night, depending on the degree of irregularity, are referred to as the sleep disordered breathing, sleep apnea or hypopnea. Irregular or a-periodic breathing also occurs in premature newborns with immature respiratory control system and critically ill patients with respiratory instability (Cheyne-Stokes respiration in patients with heart failure or coma). FIG. 4 shows that breathing movements are associated with changes in the amplitude of the electrocardiographic R-waves. Note the high-frequency noise in the ECG signal during body movements. Changes in the amplitude of the ECG waveforms (S and T waves) associated with changes in body position are shown in FIG. 5.

Figure 6:
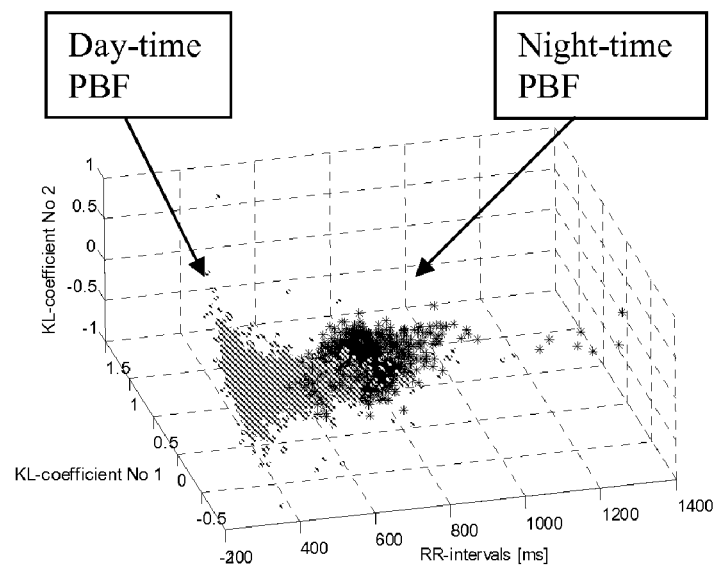
FIG. 6 plots 3-variable physiological basis functions (PBFs) obtained during daytime and nighttime in the same individual, using the series of RR-intervals, and two KL-coefficients extracted from the time series of repolarization segments (the electrocardiographic STT complexes).

FIG. 6 is an example of the daytime and nighttime physiological basis functions (PBFs) constructed using the series of RR-intervals, and two KL-coefficients extracted from the time series of repolarization segments (the electrocardiographic STT complexes). Note that the two PBFs are clearly separated in this 3-variable space, which shows physiological differences between the nighttime and daytime electrophysiological dynamics.

Figure 7:
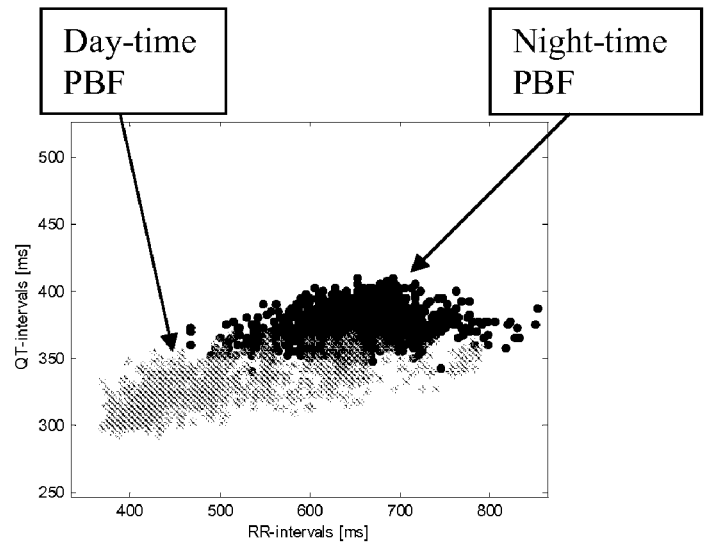
FIG. 7 plots the daytime and nighttime physiological basis functions constructed using the series of electrocardiographic RR- and QT-intervals.

FIG. 7 is an example of the daytime and nighttime physiological basis functions (PBFs) constructed using the series of RR- and QT-intervals. Although these 2 PBFs are not clearly separated in the 2-dimensional space, they show some differences between the nighttime and daytime electrophysiological activity.

Figure 8:
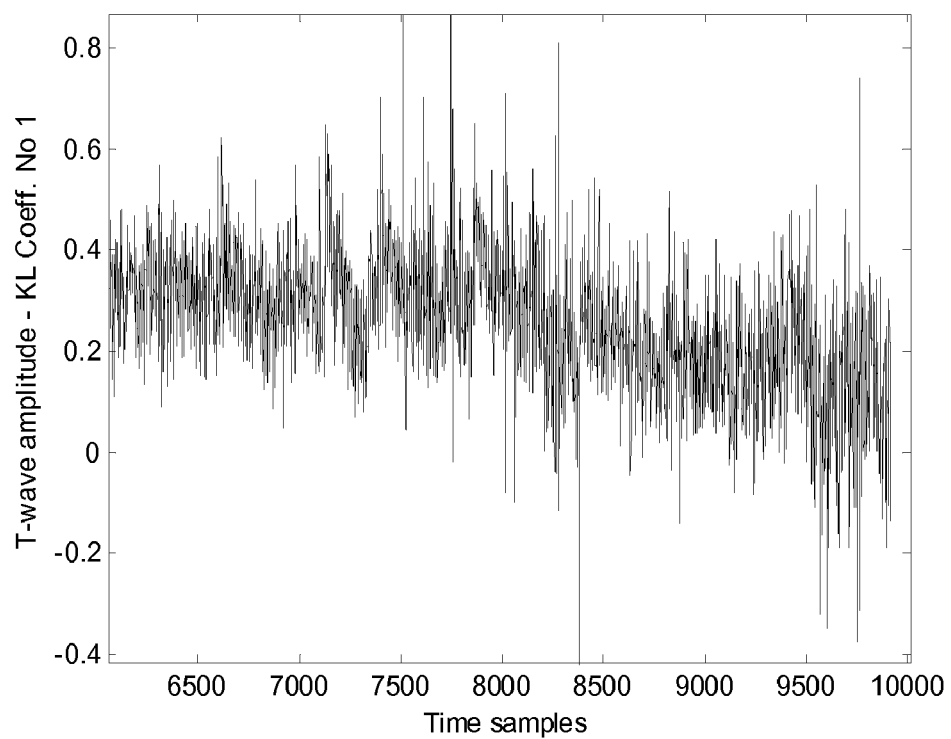
FIG. 8 plots the difference between the time series of electrocardiographic T-waves obtained during morning hours and the corresponding Karhunen-Loeve coefficients No 1 and No 2 obtained from the 24-hour time series of T-wave amplitudes in this human subject.
Figure 8:
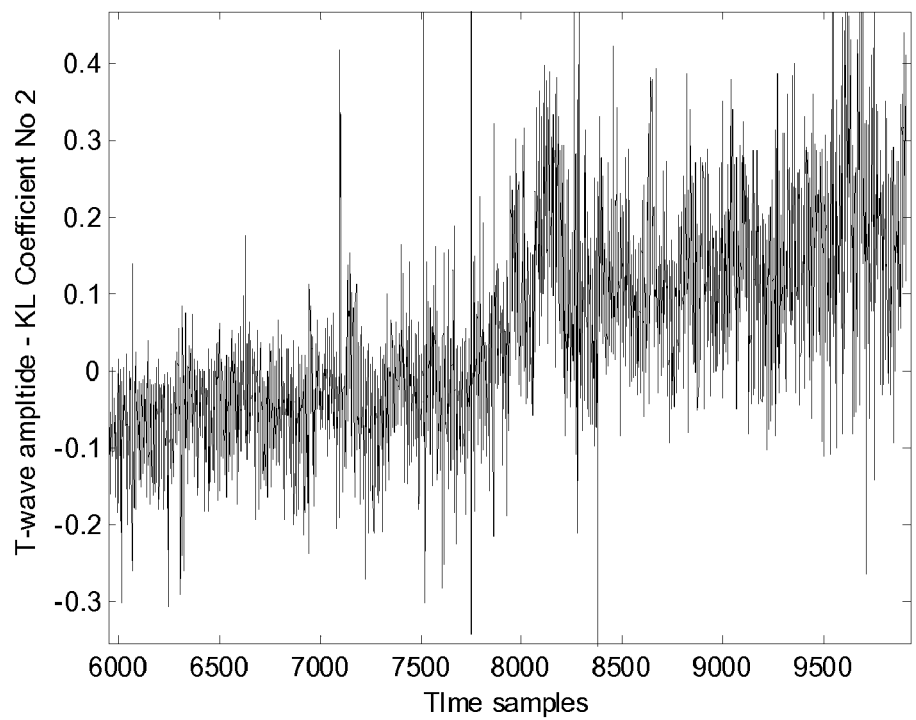

FIG. 8 plots the difference between the time series of electrocardiographic T-waves obtained during morning hours and the corresponding Karhunen-Loeve coefficients No 1 and No 2 obtained from the 24-hour time series of T-wave amplitudes in this human subject. It shows increased randomness and abrupt disturbances in the time series of electrocardiographic T waves during morning hours quantified as the distance (difference) between the time series of T-wave amplitudes and the $1^{nd}$ and $2^{nd}$ Karhunen-Loeve coefficients of the corresponding time series. These Karhunen-Loeve coefficients are associated with the eigenvectors representing most of the energy (variance) of the signal; therefore, these coefficients can be considered as PBFs, representing characteristic features/patterns of the data.

Figure 9:
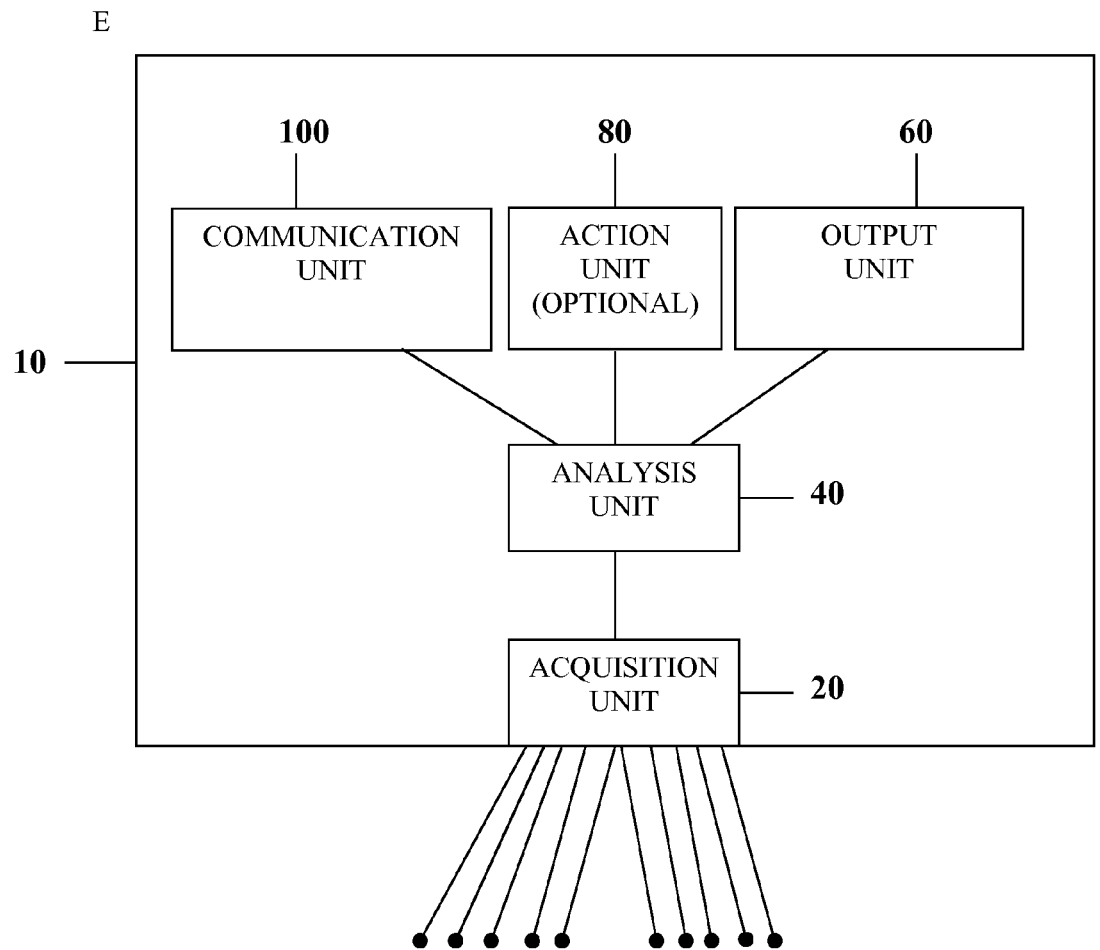
FIG. 9 is a block diagram of the multi-scale (multi-resolution, multi-level, multi-layer) method and system of the preferred embodiment of this invention.
Figure 10:
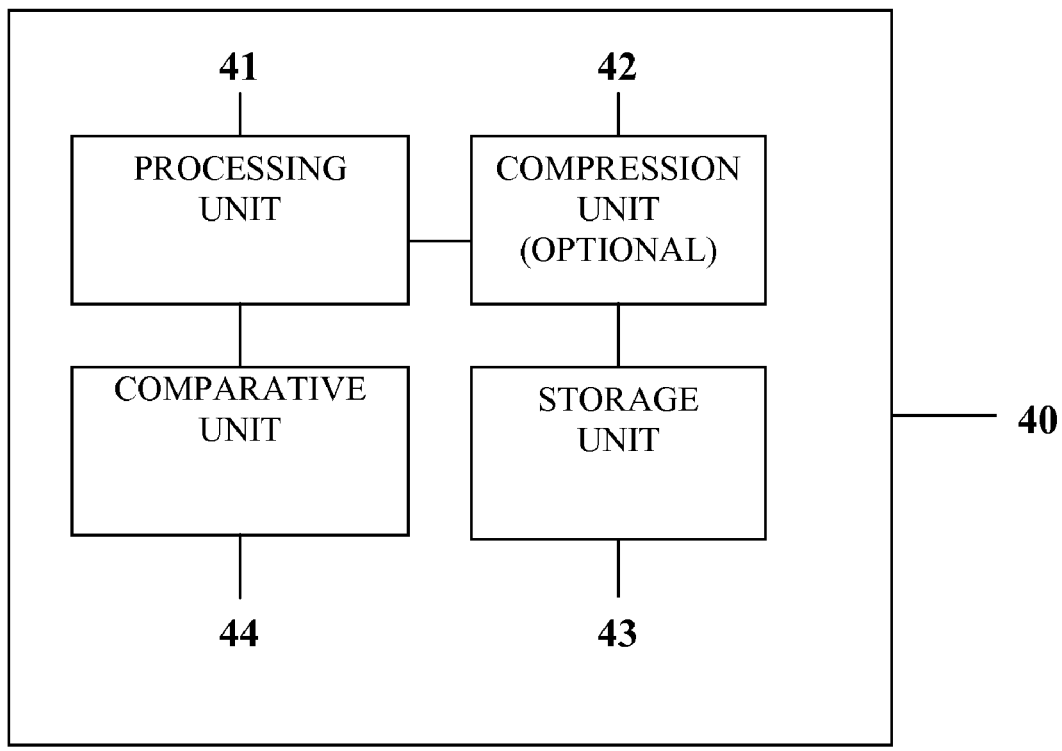
FIG. 10 is a block diagram of the analysis unit of a physiological monitoring system (for example, an electrocardiographic, ECG system), which is interfaced with the first level of the system of the present invention (to incorporate the ECG data, processed or unprocessed).

FIG. 9 is a block-diagram of a preferred embodiment of a system for at least one of information management, decision support, diagnosis, examination (physical, physiological, biochemical, etc.), monitoring, advice, medical recommendation, and bi-directional communication between individuals (patients), medical professionals (physicians, nurses, technicians) and medical centers. The system may receive physiological or health data (for example, ECG data) from a recorded data source for analysis, but preferably receives the data real-time, on-line. As used herein, patient means an animal, and most likely a human. The medical device further includes an analysis unit or module 40 which, in turn, consists of processing, compression, storage, and comparison units (FIG. 10). The processing unit 41 can be a typical computer or personal computer of the type available from many vendors such as IBM or Hewlett-Packard. The processing unit 41 is programmed to detect a plurality of characteristic points such as the onset, peak and offset of P-, Q-, R-, S-, T-, U-waves, and computes the characteristic parameters or primary elements which include amplitudes of the said waves and ST-segment, duration of PQ-, QRS-, and QT-intervals. The processing unit 41 has a programmable microprocessor that can be programmed to modify or change the set of primary elements or to adjust their search criteria. This allows individual adjustment of the characteristic points which, in turn, increases the accuracy of detection of the primary elements. For instance, in signals with biphasic T-wave, two T-peaks should be detected, whereas monophasic T-wave requires detection of a single T-peak. Furthermore, the criteria for determining the offset of biphasic T-wave are different from the criteria for the offset of monophasic T-wave. Individual adjustment of the primary elements and their search criteria increases the accuracy of the detection of characteristic points in different ECG patterns. Still another possibility is analysis of combined changes in some primary elements or disabling analysis of the other elements. For example, in patients with possible electrolyte abnormalities, the amplitudes of the T-wave and U-wave may be combined into a single index which will be convenient for monitoring. Furthermore, the set of monitored primary elements can be modified according to the specifics of cardiovascular abnormality. For example, in patients with coronary artery disease, the amplitude and the slope of the ST-segment should be monitored continuously. However, its initial or chronic displacement (e.g., chronic ST-depression) might require an individual threshold adjustment to improve separation of chronic from acute changes.

Figure 11:
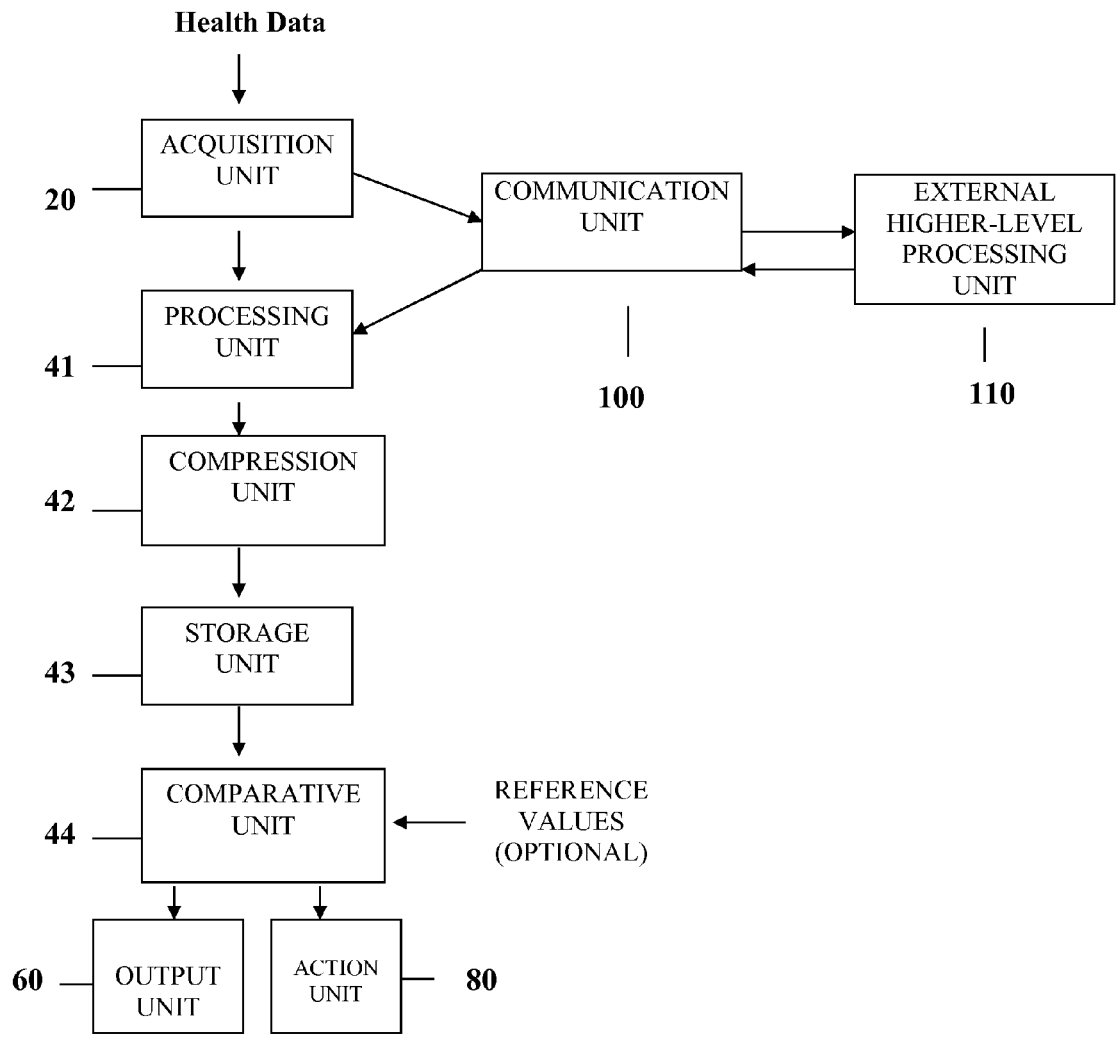
FIG. 11 is a flowchart of operation of the preferred embodiment.

FIG. 11 is a flowchart of the operation of the preferred embodiment. Compression unit 42 compresses the ECG waveform into a few weighted basis vectors and their coefficients using principal component analysis, wavelet decomposition, or other orthogonal mathematical transformation. Storage unit 43 stores the compressed waveforms and the computed primary elements into memory. Comparative unit 44 compares the newly acquired waveforms and newly computed primary elements with the waveforms and primary elements previously stored in the storage unit 43. The analysis unit 40 has means for adjusting the thresholds for each indicator, whereas the default values correspond to normal ECG. An output unit 60 includes a screen or a set of indicators for displaying the ECG waveforms and the computed primary elements in comparison with the previously stored primary elements or in comparison with the default reference values. The results of comparison can be represented both qualitatively and quantitatively in the dynamic and static modes. Abnormal readings may be further classified into moderately abnormal and severely abnormal. To make the indicators understandable to a lay person, the degree of abnormality may be color-coded: green color corresponds to a normal value, yellow corresponds to a moderate abnormality, and red corresponds to a severe abnormality. In the dynamic mode, the quantitative representation shows the differences between the newly acquired and stored primary elements and waveforms, whereas the qualitative representation includes indication of each parameter as being changed (C) or unchanged (U). The output unit 60 may alternatively or additionally feed an output data to an action unit 80 for sounding an alarm, generating a vibration, or taking appropriate measures, such as applying the drugs or adjusting the therapy mode. Communication unit 100 transmits the information between the device 10 and external higher-level processing device 110. The communication unit 100 may be a modem or a wireless transmitter/receiver. Electrocardiographic signals and recorded values of primary elements and indexes are transmitted from the device 10 to higher level devices for more detailed processing and storage. The higher-level device 110 preferably transmits back to device 10 a set of primary elements and their search criteria to be used in device 10.

EXAMPLE 1

Application of PBFs for in-Hospital Post-Operative, Critical Care and Emergency Settings One example of a potential application of PBFs is for improved patient management in the post-operative, critical care and emergency care settings. As a standard of clinical care, patients after cardiac transplantation are routinely placed under continuous 24-hour observation and bedside monitoring in a post-operative intensive care unit. The data collected during such monitoring can be sent (using wireless or wire-type connection) for processing to the electronic medical record (EMR) system, which can also perform comparison of newly acquired data with each individual's PBFs obtained during previous, consecutive 24-hour periods of monitoring. In this hypothetical example, comparison with the individual's PBFs can expose subtle changes in the patterns of fever, heart rate, and post-operative blood count during the 24-hour period. These subtle changes cannot be exposed by traditional methods that use comparisons with population-based threshold values. When such subtle serial changes are detected, the EMR system can generate an alert for an attending physician, prompting the physician to administer additional tests, which can expose an early, sub-clinical stage of sepsis. As a result, an aggressive antibiotic therapy can be immediately started to avert further progression of sepsis. Captured at the earliest stages, the sepsis can be effectively treated within the shortest possible time, preventing life-threatening complications and shortening the time of the hospital stay.

EXAMPLE 2

Application of PBFs for Improving the Efficacy of Clinical Trials

Analysis of serial changes in patients' health plays an important role in the assessment of clinical study progress and results. In this hypothetical example, a mobile, high-fidelity 12-lead ECG monitor with wireless network connectivity could have been employed by the clinical study investigators evaluating cardiac safety of a new pharmaceutical agent. The mobile system collects information regarding patients' body position and respiration, in addition to the high-fidelity 12-lead electrocardiogram. The data could be recorded and transmitted wirelessly via a cell phone line to a secure Internet site, which can automatically identify each patient in its database, compare the newly acquired data with previously obtained from the same patient PBFs and store the results of the comparisons in its database.

Since the individuals' PBFs provide more accurate baseline "templates" then population-based estimates, changes in the QT-intervals and T-wave morphology can be detected earlier. In addition, the inclusion of data on respiratory movements and body position further improves the accuracy of PBF-based comparisons (by selecting the ECG data and PBFs obtained during matching parts of respiratory cycles, for example during the peak of the inhaling phase or exhaling phase of the respiratory cycle). This, in turn, can significantly reduce the amount of noise and variability in the serial data patterns, allowing earlier identification of trends in the data, which cannot be exposed by conventional methods. Thus, the PBF-based, individually-tailored analysis can allow more efficient analysis of serial data, resulting in earlier identification of data trends, which in turn reduces the number of participants, as well as time and cost associated with clinical trials.

EXAMPLE 3

Application of PBFs for Mobile Monitoring and Cardiovascular Safety During Exercises Physical exercises represent an important tool for maintaining cardiovascular health and fitness. However, they also represent a high-risk period with a number of life-threatening complications that occur due to unusually high stress on the cardiovascular system. A number of life-threatening cardiac arrhythmias, ischemic events and stroke have been reported during exercises even in high-level athletes. In this hypothetical example, a marathon runner is monitored by a mobile, wireless system that monitors an ECG and physical activity. The system extracts the primary elements representing the most important information contained in the ECG signal (the amplitudes and durations of P, Q, R, S, T, and U-waves, and ST, PQ, and QT segments) and compares them to reference values obtained from the individual's PBFs. The PBFs can be derived either locally, in the monitor, using software installed on a cell phone or remotely on an Internet server. In the latter scenario, the data and/or primary elements are sent from the cell phone to the remote Internet server for comparison with the individual's PBFs, whereas the server sends the updated threshold parameters derived from the individual's PBFs back to the individual's cell phone.

During the marathon practice, the pattern of heart rate and ST-segment could demonstrate significant (>3 standard deviations) difference compared with the individual's PBFs recorded during previous runs of similar intensity (the speed or intensity of the exercise is also monitored by a monitoring system using a 3-axial accelerometer and these data are incorporated within the corresponding PBF). This subtle but potentially life-threatening deviation in the pattern of serial data cannot be exposed by conventional methods. However, once a system of this invention identifies a significant deviation from the individual's PBF, within a few seconds it forwards this information to a healthcare professional, who recommends that the runner stops physical activity and comes for cardiovascular evaluation. During the tests, a significant narrowing of a major coronary artery can be discovered, prompting urgent catheterization and angioplasty, which can avert potentially life-threatening ischemia.

EXAMPLE 4

Advantages of Using PBFs in the Home Environment

This hypothetical example demonstrates advantages of using PBFs for home monitoring. In this example, an individual with chronic heart failure, obesity and type II diabetes uses a home-based data management system, which collects data from multiple sensors and visualization of trends or serial changes in such data over time, to allow medical professionals monitor changes from a remote location and make adjustments in medications and other forms of treatment. In addition, the data management system also visualizes the serial trends to the patient, to encourage his/her active participation in the treatment and healthcare management. However, the data management system cannot analyze such serial dynamics and cannot determine which changes are clinically important.

Incorporating analysis of serial dynamics disclosed in Shusterman patents facilitates more accurate detection and classification of serial changes, which in turn, would lead to more accurate and timely adjustments of treatment, including changes in the dose and type of medications, as well as earlier detection of deterioration in patient's condition requiring hospitalization, cardiac catheterization or other emergency procedures. It also facilitates timely detection of life-threatening instabilities and precursors of serious complications, as well as treatment-related side-effects. Furthermore, incorporating PBFs into the analysis to provide more accurate, personalized baseline/reference for each physiological activity and their transitions will further increase the accuracy of serial monitoring and early detection of deterioration in someone's health and serious complications.

In this example, if an elderly individual at home has gradual changes in blood pressure, they would be missed by conventional methods, which do not use personalized PBFs. However, the PBF-base analysis will accurately detect such changes at the earliest stages and forward this information to a healthcare professional, who can adjust the dose of antihypertensive medications, thus preventing life-threatening complications, including a stroke.

EXAMPLE 5

Advantages of PBFs for Implantable Devices

An increase in the number of implantable sensors and their data transmission capabilities has led to rapid proliferation of implantable devices, allowing monitoring of trends and serial changes in patient's data. In this hypothetical example, a patient has an implanted sensor monitoring trends in the intra-thoracic impedance. Currently, implantable devices can employ only a simplified adjustment of the monitoring thresholds using individual's historical data. The accuracy of such a simplified analysis can be significantly improved by incorporating multi-scale, PBF-based analysis, as shown in this hypothetical example.

In this example, if the patient exhibits subtle reduction in the transthoracic impedance (an indirect indicator of increased fluid volume in the lungs, also referred to as the pulmonary edema) during the transition from sleep to regular daily activities, these changes would be missed by the simplified threshold adjustment algorithms employed by current implantable systems, because they take into account only a few parameters of the historical trends. In contrast, the PBF-based serial analysis facilitates more accurate comparison of the patient's newly acquired data with his/her historical data obtained during the same physiological activity, thus allowing more accurate detection of subtle trends. This timely detection of changes in a patient's pulmonary fluid volume, in turn, will allow timely adjustment of patient management.

Whereas particular aspects of the method of the present invention and particular embodiments of the invention have been described for purposes of illustration, it will be appreciated by those skilled in the art that numerous variations of the details may be made without departing from the invention as described in the appended claims.

What is claimed is:

1. A method useful in healthcare information management comprising:
 collecting at least one primary element as a snapshot present at the time of recording of health data using at least one collection method selected from one-time, periodic, quasi-periodic and continuous monitoring, and electronically comparing said at least one primary element with at least one reference value selected from physiological basis functions representing physiological and pathophysiological states, and transitions between said physiological and pathophysiological states to detect changes in said at least one primary element and thereby identify any abnormal or unstable primary element (a first-level, low-resolution analysis); and analyzing serial changes in said at least one primary element of health data using a dynamic serial analysis and processing unit employing at least one of the following methods selected from mathematical decomposition, mathematical modeling, computer modeling, signal processing, time-series analysis, statistical analysis, and methods of artificial intelligence for assessing changes in serial data, orthogonal decomposition, non-orthogonal decomposition (independent component analysis), multidimensional scaling based on non-metric distances and mapping techniques, non-orthogonal linear mappings, nonlinear mappings and other methods, that make use of projection, re-scaling (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability, Bayesian network, Euclidean, Markov model, hidden Markov model, and Mahalanobis distance, pattern recognition, fuzzy logic, neural networks, expert systems, and hybrid artificial intelligence systems to provide detailed characterization of serial changes in any abnormal or unstable primary element (a second-level, higher resolution serial analysis).

2. A method as set forth in claim 1 in which said physiological basis functions are adapted for representing a sequence of at least two physiological states with a transition between them represented by at least one of Markov and hidden Markov model with a transition probability matrix.

3. A method as set forth in claim 1 in which said physiological and pathophysiological states are selected from sleep, REM-sleep, non-REM sleep, wakefulness, physical activity, food intake, mental activity, exercise, physical exercise, mental stress and different body positions, including standing, sitting and supine position.

4. A method as set forth in claim 1 in which said physiological and pathophysiological states are adjusted for seasonal, circadian, geographical, environmental factors, age, sex, medical history, medications, genetic, biochemical, biophysical, physiological, occupational factors.

5. A method as set forth in claim 1 in which said physiological basis functions are adapted for at least one of remote monitoring at home or in a hospital, guiding healthcare management, tracking disease progression from one phase to another, classifying and tracking changes in health status through a sequence of health states, identifying the time of day associated with collected data, segmenting the data into different physiological periods, including REM and non-REM sleep, wakefulness, exercise, mental stress, work, rest, food intake, segmenting the data into pathophysiological states of disease progression, including identification of heart failure class, shock or sepsis severity, treatment and side-effect control; health, fitness and wellness guide; prediction and management of psychological stress, forecasting high-risk periods, optimizing treatment schedule, optimizing physical fitness schedule, subject identification, and efficient analysis of serial data collected in the course of a clinical trial;

identification of a library of physiological templates for improved detection of physiological waves and events, which include electrocardiographic P, Q, R, S, T and U-waves, blood pressure waves, vascular activity waves, cardiac output dynamics, intra-thoracic fluid, electrical activation sequence of the heart, electrical repolarization sequence of the heart, and mechanical activation sequence of the heart.

6. A method as set forth in claim 1 in which said physiological basis functions are constructed by fusion of different data types of health data, including electrocardiogram, blood pressure, cardiac output, vascular activity, transthoracic impedance, electroencephalogram, muscular activity, temperature, blood count, physical activity and other biochemical, hormonal, biophysical, genetic, proteomic types of data.

7. A method as set forth in claim 1 in which said collecting at least one primary element and electronically comparing said at least one primary element with at least one reference value to detect changes in said at least one primary element and thereby identify any abnormal or unstable primary element (a first-level, low-resolution analysis) of health data is performed repeatedly over time.

8. A method as set forth in claim 7 in which said healthcare information is collected and analyzed substantially continuously for a period in a range of at least several minutes to many days.

9. A method as set forth in claim 1 that includes personalized adaptation of diagnostic criteria.

10. A method as set forth in claim 1 in which analyzing said data to provide detailed characterization of serial changes in said abnormal or unstable primary elements is selected from a fuzzy-logic classifier and a dynamic neural network with at least one neuron (unit) analyzing changes in at least one state of activity of at least one physiological, biochemical, biophysical, mechanical, and genetic system relative to at least one reference value.

11. A method as set forth in claim 1 in which said first-level analysis and said second-level analysis exchange information using a wireless communication device selected from at least one of a cell phone, smart phone, PDA, Wi-Fi, and other types of radio-transmitters and communication devices.

12. A method as set forth in claim 1, in which said analyzing serial changes is applied to physiological signals selected from at least one of electrocardiogram, electroencephalogram, magnetocardiogram, pulse oximetry, impedance, magnetic resonance (MRI), computed tomography (CT), ultrasound, fluoroscopic, X-ray imaging, stress-test, physical activity, clinical symptoms, chest pain, shortness of breath, nausea, blood pressure, cardiac output, vascular activity, temperature, respiration, cardiac, abdominal, or breathing sounds, blood flow, hormonal concentration, physical activity, blood tests, weight, heart rate, enzyme and protein level, genetic, genomic, proteomic, metabolomic, and molecular data, neural activity, electroencephalographic activity, and other electrical, mechanic, sonic, biochemical, biophysical processes in the human body, demographic, psychological, and environmental data.

13. A method as set forth in claim 1 in which at least one of information completeness and a probability of a certain disease is tracked dynamically in at least one level of analysis.

14. A system useful in healthcare information management comprising:

a first analysis and processing unit for analyzing a snapshot of at least one of a plurality of primary elements from recorded health data and processing said at least one primary element to generate data respecting said at least one primary element, and comparing at least one reference value selected from physiological basis functions representing physiological and pathophysiological states, and transitions between said physiological and pathophysiological states respecting said at least one primary element with data newly received by said first analysis and processing unit and producing at least one indicator respecting any differences between said at least one reference value and said newly received data (a low resolution analysis), a second analysis and processing unit that includes at least one computer device of higher resolution analysis for processing health data collected over time using at least one of the following methods selected from mathematical decomposition, mathematical modeling, computer modeling, signal processing, time-series analysis, statistical analysis, and methods of artificial intelligence for assessing changes in serial data, orthogonal decomposition, non-orthogonal decomposition (independent component analysis), mathematical modeling, computer modeling, signal processing, time-series analysis, statistical analysis, multidimensional scaling based on non-metric distances and mapping techniques, non-orthogonal linear mappings, nonlinear mappings and other methods, that make use of projection, re-scaling (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability, Bayesian network, Euclidean, Markov model, hidden Markov model, and Mahalanobis distance, pattern recognition, fuzzy logic, neural networks, expert systems, and hybrid artificial intelligence systems to detect serial changes in said at least one primary element (higher resolution analysis); and in which said at least one of first analysis and processing unit and said at least one computer device for a higher resolution analysis performs at least one analysis selected from forecasting or prediction of serial changes or trends in physiological or health data, early prediction and prevention of physiological disorders and abnormalities, assessment of short-term and long term dynamics, fitness level, disease progression, treatment, complications and side-effects control, assessment of clinical trials data, physical examination, early detection of subtle changes, timely initiation of therapy, adjustment of therapy, comparison of the values of data obtained from individual patients against values obtained from at least one of a group of patients and a population of patients to facilitate analysis of individual data and to determine the values that characterize said at least one of a group of patients and a population of patients with similar characteristics and similar disorders.

15. A system as set forth in claim 14 which includes at least one acquisition unit for collecting data using at least one collection method selected from one-time, periodic, quasi-periodic and continuous monitoring.

16. A system as set forth in claim 15 in which said at least one acquisition unit is implantable.

17. A system as set forth in claim 14 in which said second analysis and processing unit is connected to several computers via a computer network for at least one of visualization and analysis of the health data.

18. A system as set forth in claim 14 in which at least one of said first analysis and processing unit and said at least one computer device analyze physiological data selected from at least one of electrocardiogram, electroencephalogram, magnetocardiogram, pulse oximetry, impedance, magnetic resonance (MRI), computed tomography (CT), ultrasound, fluoroscopic, X-ray imaging, stress-test, physical activity, clinical symptoms, chest pain, shortness of breath, nausea, blood pressure, cardiac output, vascular activity, temperature, respiration, cardiac, abdominal, or breathing sounds, blood flow, hormonal concentration, physical activity, blood tests, weight, heart rate, enzyme and protein level, genetic, proteomic, and molecular data, neural activity, electroencephalographic activity, and other electrical, mechanic, sonic, biochemical, biophysical processes in the human body, demographic, psychological, and environmental data.

19. A system as set forth in claim 14 in which at least one of said first analysis and processing unit (low-resolution analysis unit) and said second analysis and processing unit (high-resolution analysis unit) is a wireless communication device selected from at least of one of a cell phone, smart phone, PDA, Wi-Fi, and other types of radio-transmitters and communication devices.

20. A system as set forth in claim 19 in which said communications device is adapted to continuously send at least one of information, raw data, and derived parameters to at least one of said first analysis and processing unit (low-resolution analysis unit), and second analysis and processing unit (high-resolution analysis unit).

\* \* \* \* \*